US008641775B2

(12) United States Patent
Harmon et al.

(10) Patent No.: US 8,641,775 B2

(45) **Date of Patent: *Feb. 4, 2014**

(54) VIABLE TISSUE REPAIR IMPLANTS AND METHODS OF USE

(75) Inventors: Alexander M. Harmon, Clinton, NJ (US); Stephanie M. Kladakis, Watertown, MA (US); Julia Hwang, Wayland, MA (US)

(73) Assignee: DePuy Mitek, LLC, Raynham, MA (US)

( * ) Notice: Subject to any disclaimer, the term of this patent is extended or adjusted under 35 U.S.C. 154(b) by 172 days.

This patent is subject to a terminal disclaimer.

(21) Appl. No.: 13/018,900

(22) Filed: Feb. 1, 2011

(65) Prior Publication Data

US 2011/0177134 A1 Jul. 21, 2011

Related U.S. Application Data

(63) Continuation of application No. 10/729,046, filed on Dec. 5, 2003, now Pat. No. 7,901,461.

(51) Int. Cl.
*A61F 2/02* (2006.01)

(52) U.S. Cl.
USPC .......................................... 623/23.72

(58) Field of Classification Search
USPC .................... 623/23.72–23.76, 20.32, 20.35, 623/1.38–1.54, 23.58
See application file for complete search history.

(56) References Cited

U.S. PATENT DOCUMENTS 3,272,204 A 9/1966 Artandi
3,739,402 A 6/1973 Cooley et al.
3,812,017 A 5/1974 Santangelo et al.
3,857,932 A 12/1974 Shepherd et al.
4,045,418 A 8/1977 Sinclair
4,057,537 A 11/1977 Sinclair
4,105,034 A 8/1978 Shalaby et al.
4,130,639 A 12/1978 Shalaby et al.
4,130,689 A 12/1978 Costa, Jr.
4,140,678 A 2/1979 Shalaby et al.

(Continued)

FOREIGN PATENT DOCUMENTS

AU 717552 3/1998
CA 2247158 2/1997

(Continued)

OTHER PUBLICATIONS

Albrecht et al., "Closure of Osteochondral Lesions Using Chondral Fragments and Fibrin Adhesive," *Arch. Orthop. Trauma Surg.* 101: 213-217 (1983).

(Continued)

*Primary Examiner* — Alvin Stewart

(57) ABSTRACT

Biocompatible tissue implants are provided for repairing a tissue injury or defect. The tissue implants comprise a biological tissue slice that serves as a source of viable cells capable of tissue regeneration and/or repair. The biological tissue slice can be harvested from healthy tissue to have a geometry that is suitable for implantation at the site of the injury or defect. The harvested tissue slice is dimensioned to allow the viable cells contained within the tissue slice to migrate out and proliferate and integrate with tissue surrounding the injury or defect site. Methods for repairing a tissue injury or defect using the tissue implants are also provided.

18 Claims, 7 Drawing Sheets

12 10 34 20 22
14

(56) References Cited

U.S. PATENT DOCUMENTS 4,141,087 A 2/1979 Shalaby et al.
4,205,399 A 6/1980 Shalaby et al.
4,208,511 A 6/1980 Shalaby et al.
4,344,193 A 8/1982 Kenny
4,520,821 A 6/1985 Schmidt et al.
4,553,272 A 11/1985 Mears
4,585,458 A 4/1986 Kurland
4,597,766 A 7/1986 Hilal et al.
4,609,551 A 9/1986 Caplan et al.
4,728,329 A 3/1988 Mansat
4,801,299 A 1/1989 Brendel et al.
4,837,285 A 6/1989 Berg et al.
4,902,508 A 2/1990 Badylak et al.
4,917,700 A 4/1990 Aikins
4,946,377 A 8/1990 Kovach
5,007,934 A 4/1991 Stone
5,041,138 A 8/1991 Vacanti et al.
5,053,050 A 10/1991 Itay
5,061,281 A 10/1991 Mares et al.
5,078,744 A 1/1992 Chvapil
5,108,989 A 4/1992 Amento et al.
5,147,400 A 9/1992 Kaplan et al.
5,176,708 A 1/1993 Frey et al.
5,206,023 A 4/1993 Hunziker
5,258,028 A 11/1993 Ersek et al.
5,263,984 A 11/1993 Li et al.
5,306,311 A 4/1994 Stone et al.
5,326,357 A 7/1994 Kandel
5,366,756 A 11/1994 Chesterfield et al.
5,393,594 A 2/1995 Koyfman et al.
5,425,766 A 6/1995 Bowald
5,443,950 A 8/1995 Naughton et al.
5,445,833 A 8/1995 Badylak et al.
5,455,041 A 10/1995 Genco et al.
5,464,929 A 11/1995 Bezwada et al.
5,468,253 A 11/1995 Bezwada et al.
5,480,827 A 1/1996 Guillemin et al.
5,487,897 A 1/1996 Polson et al.
5,514,181 A * 5/1996 Light et al. ................ 623/13.18
5,514,378 A 5/1996 Mikos et al.
5,571,189 A 11/1996 Kuslich
5,577,517 A 11/1996 Bonutti
5,589,176 A 12/1996 Seare, Jr.
5,595,751 A 1/1997 Bezwada et al.
5,597,579 A 1/1997 Bezwada et al.
5,607,687 A 3/1997 Bezwada et al.
5,612,028 A 3/1997 Sackier et al.
5,618,552 A 4/1997 Bezwada et al.
5,620,698 A 4/1997 Bezwada et al.
5,624,463 A 4/1997 Stone et al.
5,632,745 A 5/1997 Schwartz
5,645,850 A 7/1997 Bezwada et al.
5,648,088 A 7/1997 Bezwada et al.
5,654,135 A 8/1997 Tinois et al.
5,656,492 A 8/1997 Glowacke et al.
5,677,355 A 10/1997 Shalaby et al.
5,681,353 A 10/1997 Li et al.
5,697,976 A 12/1997 Chesterfield et al.
5,698,213 A 12/1997 Jamiolkowski et al.
5,700,583 A 12/1997 Jamiolkowski et al.
5,705,181 A 1/1998 Cooper et al.
5,709,854 A 1/1998 Griffith-Cima et al.
5,711,960 A 1/1998 Shikinami
5,720,969 A 2/1998 Gentile et al.
5,723,331 A 3/1998 Tubo et al.
5,735,903 A 4/1998 Li et al.
5,736,372 A 4/1998 Vacanti et al.
5,755,791 A * 5/1998 Whitson et al. ................ 623/1.1
5,759,190 A 6/1998 Vibe-Hansen et al.
5,766,631 A 6/1998 Arnold
5,769,899 A 6/1998 Schwartz et al.
5,786,217 A 7/1998 Tubo et al.
5,800,543 A 9/1998 McLeod et al.
5,830,493 A 11/1998 Yokota et al.
5,837,235 A 11/1998 Mueller et al.
5,842,477 A * 12/1998 Naughton et al. ............ 128/898
5,855,608 A * 1/1999 Brekke et al. ................. 424/487
5,859,150 A * 1/1999 Jamiolkowski et al. ...... 525/437
5,891,558 A 4/1999 Bell et al.
5,902,741 A 5/1999 Purchio et al.
5,904,716 A 5/1999 Gendler
5,904,717 A 5/1999 Brekke et al.
5,914,121 A 6/1999 Robey et al.
5,922,025 A * 7/1999 Hubbard ....................... 424/423
5,964,805 A 10/1999 Stone
5,968,096 A * 10/1999 Whitson et al. ............... 424/423
5,980,889 A 11/1999 Butler et al.
5,989,269 A 11/1999 Vibe-Hansen et al.
5,990,194 A 11/1999 Dunn et al.
5,990,378 A 11/1999 Ellis
6,001,352 A 12/1999 Boyan et al.
6,001,394 A 12/1999 Daculsi et al.
6,005,161 A 12/1999 Brekke et al.
6,027,742 A 2/2000 Lee et al.
6,042,610 A 3/2000 Li et al.
6,054,122 A 4/2000 MacPhee et al.
6,077,989 A 6/2000 Kandel et al.
6,080,579 A 6/2000 Hanley, Jr. et al.
6,096,532 A 8/2000 Armstrong et al.
6,103,255 A * 8/2000 Levene et al. ................. 424/426
6,110,209 A 8/2000 Stone
6,110,212 A * 8/2000 Gregory ..................... 623/23.72
6,117,166 A 9/2000 Winston et al.
6,120,514 A 9/2000 Vibe-Hansen et al.
6,121,042 A 9/2000 Peterson et al.
6,123,727 A 9/2000 Vacanti et al.
6,132,463 A 10/2000 Lee et al.
6,132,468 A 10/2000 Mansmann
6,139,578 A 10/2000 Lee et al.
6,140,039 A * 10/2000 Naughton et al. ............. 435/1.1
6,143,293 A 11/2000 Weiss et al.
6,153,292 A 11/2000 Bell et al.
6,156,068 A 12/2000 Walter et al.
6,165,217 A 12/2000 Hayes
6,176,880 B1 1/2001 Plouhar et al.
6,179,840 B1 1/2001 Bowman
6,179,872 B1 1/2001 Bell et al.
6,180,007 B1 1/2001 Gentile et al.
6,183,737 B1 2/2001 Zaleske et al.
6,187,053 B1 2/2001 Minuth
6,187,329 B1 2/2001 Agrawal et al.
6,197,061 B1 3/2001 Masuda et al.
6,197,325 B1 3/2001 MacPhee et al.
6,200,606 B1 3/2001 Peterson et al.
6,214,045 B1 4/2001 Corbitt, Jr. et al.
6,214,055 B1 4/2001 Simionescu et al.
6,242,247 B1 6/2001 Rieser et al.
6,251,673 B1 6/2001 Winkler
6,277,151 B1 8/2001 Lee et al.
6,283,980 B1 9/2001 Vibe-Hansen et al.
6,287,340 B1 9/2001 Altman et al.
6,291,240 B1 9/2001 Mansbridge et al.
6,306,177 B1 10/2001 Felt et al.
6,306,424 B1 10/2001 Vyakarnam et al.
6,316,692 B1 11/2001 Readhead et al.
6,319,712 B1 11/2001 Meenen et al.
6,331,312 B1 12/2001 Lee et al.
6,333,029 B1 12/2001 Vyakarnam et al.
6,365,149 B2 4/2002 Vyakarnam et al.
6,378,527 B1 4/2002 Hungerford et al.
6,378,572 B1 4/2002 Neubauer et al.
6,379,367 B1 4/2002 Vibe-Hansen et al.
6,464,729 B1 10/2002 Kandel
6,485,723 B1 * 11/2002 Badylak et al. .............. 424/93.7
6,489,165 B2 12/2002 Bhatnagar et al.
6,511,958 B1 1/2003 Atkinson et al.
6,521,430 B1 * 2/2003 Orwar et al. ............... 435/173.6
6,530,956 B1 3/2003 Mansmann
6,534,084 B1 * 3/2003 Vyakarnam et al. .......... 424/443
6,541,024 B1 4/2003 Kadiyala et al.
6,551,355 B1 4/2003 Lewandrowski et al.
6,569,172 B2 5/2003 Asculai et al.
6,592,588 B1 * 7/2003 Bobic et al. ..................... 606/79
6,599,323 B2 * 7/2003 Melican et al. ............ 623/23.72

(56) References Cited

U.S. PATENT DOCUMENTS

| | | | | |
|---|---|---|---|---|
| 6,605,294 | B2 * | 8/2003 | Sawhney | 424/426 |
| 6,626,950 | B2 * | 9/2003 | Brown et al. | 623/23.72 |
| 6,727,224 | B1 * | 4/2004 | Zhang et al. | 514/8.8 |
| 6,773,458 | B1 * | 8/2004 | Brauker et al. | 623/11.11 |
| 6,783,712 | B2 * | 8/2004 | Slivka et al. | 264/51 |
| 6,840,962 | B1 * | 1/2005 | Vacanti et al. | 623/23.76 |
| 6,852,330 | B2 * | 2/2005 | Bowman et al. | 424/426 |
| 6,866,681 | B2 * | 3/2005 | Laboureau et al. | 623/13.2 |
| 6,884,428 | B2 * | 4/2005 | Binette et al. | 424/422 |
| 6,886,568 | B2 * | 5/2005 | Frondoza et al. | 128/898 |
| 6,886,569 | B2 * | 5/2005 | Chervitz et al. | 128/898 |
| 7,109,034 | B2 * | 9/2006 | Orwar et al. | 435/461 |
| 7,208,177 | B2 * | 4/2007 | Geistlich et al. | 424/484 |
| 7,262,020 | B2 * | 8/2007 | Hellerstein | 435/29 |
| 7,316,822 | B2 * | 1/2008 | Binette et al. | 424/549 |
| 7,368,124 | B2 | 5/2008 | Chun et al. | |
| 7,456,012 | B2 * | 11/2008 | Ryttsen et al. | 435/285.2 |
| 7,824,701 | B2 * | 11/2010 | Binette et al. | 424/423 |
| 7,875,296 | B2 * | 1/2011 | Binette et al. | 424/549 |
| 7,901,461 | B2 * | 3/2011 | Harmon et al. | 623/23.72 |
| 8,137,686 | B2 | 3/2012 | Kladakis et al. | |
| 8,137,702 | B2 * | 3/2012 | Binette et al. | 424/549 |
| 8,197,837 | B2 | 6/2012 | Jamiolkowski et al. | |
| 8,221,780 | B2 | 7/2012 | Dhanaraj et al. | |
| 8,226,715 | B2 | 7/2012 | Hwang et al. | |
| 8,496,970 | B2 | 7/2013 | Binette et al. | |
| 2001/0014475 | A1 * | 8/2001 | Frondoza et al. | 435/366 |
| 2001/0016353 | A1 * | 8/2001 | Janas et al. | 435/395 |
| 2001/0016772 | A1 * | 8/2001 | Lee et al. | 623/14.12 |
| 2001/0023373 | A1 * | 9/2001 | Plouhar et al. | 623/23.72 |
| 2001/0038848 | A1 * | 11/2001 | Donda et al. | 424/423 |
| 2001/0039453 | A1 * | 11/2001 | Gresser et al. | 623/17.11 |
| 2001/0051834 | A1 * | 12/2001 | Frondoza et al. | 623/23.72 |
| 2001/0053353 | A1 * | 12/2001 | Griffith et al. | 424/93.7 |
| 2001/0053839 | A1 * | 12/2001 | Noishiki et al. | 527/300 |
| 2002/0006428 | A1 * | 1/2002 | Mahmood et al. | 424/423 |
| 2002/0009477 | A1 * | 1/2002 | Mahmood et al. | 424/423 |
| 2002/0009805 | A1 * | 1/2002 | Nevo et al. | 435/366 |
| 2002/0009806 | A1 * | 1/2002 | Hicks, Jr. | 435/391 |
| 2002/0013627 | A1 * | 1/2002 | Geistlich et al. | 623/23.63 |
| 2002/0015719 | A1 * | 2/2002 | Kellner et al. | 424/423 |
| 2002/0022883 | A1 * | 2/2002 | Burg | 623/8 |
| 2002/0022884 | A1 * | 2/2002 | Mansmann | 623/14.12 |
| 2002/0028192 | A1 * | 3/2002 | Dimitrijevich et al. | 424/93.7 |
| 2002/0029055 | A1 * | 3/2002 | Bonutti | 606/170 |
| 2002/0062151 | A1 * | 5/2002 | Altman et al. | 623/13.17 |
| 2002/0082631 | A1 * | 6/2002 | Bonutti | 606/170 |
| 2002/0083479 | A1 * | 6/2002 | Winston et al. | 800/14 |
| 2002/0091403 | A1 * | 7/2002 | Bonutti | 606/167 |
| 2002/0091406 | A1 * | 7/2002 | Bonutti | 606/192 |
| 2002/0099401 | A1 * | 7/2002 | Bonutti | 606/170 |
| 2002/0099448 | A1 * | 7/2002 | Hiles et al. | 623/23.61 |
| 2002/0107570 | A1 * | 8/2002 | Sybert et al. | 623/13.17 |
| 2002/0119177 | A1 * | 8/2002 | Bowman et al. | 424/423 |
| 2002/0120348 | A1 | 8/2002 | Melican et al. | |
| 2002/0123750 | A1 | 9/2002 | Eisermann et al. | |
| 2002/0127265 | A1 * | 9/2002 | Bowman et al. | 424/426 |
| 2002/0133229 | A1 * | 9/2002 | Laurencin et al. | 623/13.17 |
| 2002/0133235 | A1 * | 9/2002 | Hungerford et al. | 623/23.63 |
| 2002/0150604 | A1 * | 10/2002 | Yi et al. | 424/426 |
| 2002/0151975 | A1 | 10/2002 | Farr, II et al. | |
| 2002/0173558 | A1 * | 11/2002 | Williams et al. | 523/124 |
| 2002/0176893 | A1 * | 11/2002 | Wironen et al. | 424/489 |
| 2002/0177224 | A1 * | 11/2002 | Madry et al. | 435/325 |
| 2003/0003153 | A1 * | 1/2003 | Asculai et al. | 424/484 |
| 2003/0004578 | A1 * | 1/2003 | Brown et al. | 623/23.72 |
| 2003/0012805 | A1 * | 1/2003 | Chen et al. | 424/423 |
| 2003/0023316 | A1 * | 1/2003 | Brown et al. | 623/23.72 |
| 2003/0026787 | A1 * | 2/2003 | Fearnot et al. | 424/93.7 |
| 2003/0027332 | A1 | 2/2003 | Lafrance et al. | |
| 2003/0033021 | A1 * | 2/2003 | Plouhar et al. | 623/23.57 |
| 2003/0033022 | A1 * | 2/2003 | Plouhar et al. | 623/23.57 |
| 2003/0036797 | A1 * | 2/2003 | Malaviya et al. | 623/14.12 |
| 2003/0036801 | A1 * | 2/2003 | Schwartz et al. | 623/23.63 |
| 2003/0050709 | A1 * | 3/2003 | Noth et al. | 623/23.58 |
| 2003/0064917 | A1 * | 4/2003 | Crawford et al. | 514/8 |
| 2003/0075822 | A1 * | 4/2003 | Slivka et al. | 264/45.3 |
| 2003/0077311 | A1 * | 4/2003 | Vyakarnam et al. | 424/426 |
| 2003/0078617 | A1 * | 4/2003 | Schwartz et al. | 606/230 |
| 2003/0147935 | A1 | 8/2003 | Binette et al. | |
| 2003/0193104 | A1 | 10/2003 | Melican et al. | |
| 2004/0024457 | A1 * | 2/2004 | Boyce et al. | 623/13.17 |
| 2004/0059416 | A1 | 3/2004 | Murray et al. | |
| 2004/0078077 | A1 * | 4/2004 | Binette et al. | 623/13.17 |
| 2004/0078090 | A1 * | 4/2004 | Binette et al. | 623/23.76 |
| 2004/0219182 | A1 * | 11/2004 | Gomes et al. | 424/423 |
| 2004/0236424 | A1 | 11/2004 | Berez et al. | |
| 2004/0267362 | A1 | 12/2004 | Hwang et al. | |
| 2005/0002915 | A1 | 1/2005 | Atala et al. | |
| 2005/0038520 | A1 | 2/2005 | Binette et al. | |
| 2005/0048651 | A1 * | 3/2005 | Ryttsen et al. | 435/459 |
| 2005/0113937 | A1 | 5/2005 | Binette et al. | |
| 2005/0125077 | A1 | 6/2005 | Harmon et al. | |
| 2005/0147645 | A1 | 7/2005 | Budny | |
| 2005/0177249 | A1 | 8/2005 | Kladakis et al. | |
| 2005/0232967 | A1 | 10/2005 | Kladakis et al. | |
| 2005/0234549 | A1 | 10/2005 | Kladakis et al. | |
| 2006/0067967 | A1 | 3/2006 | Bowman et al. | |
| 2006/0084930 | A1 | 4/2006 | Dhanaraj et al. | |
| 2006/0204439 | A1 | 9/2006 | Hellerstein | |
| 2006/0223177 | A1 | 10/2006 | Harris et al. | |
| 2006/0280768 | A1 | 12/2006 | Hwang et al. | |
| 2006/0293760 | A1 | 12/2006 | DeDeyne | |
| 2007/0031470 | A1 | 2/2007 | Kladakis et al. | |
| 2007/0036767 | A1 | 2/2007 | Mistry et al. | |
| 2007/0250177 | A1 | 10/2007 | Bilbo | |
| 2008/0039955 | A1 | 2/2008 | Hunziker | |
| 2008/0071385 | A1 | 3/2008 | Binette et al. | |
| 2008/0226870 | A1 | 9/2008 | Sypeck et al. | |
| 2011/0009963 | A1 | 1/2011 | Binnette et al. | |
| 2011/0091517 | A1 | 4/2011 | Binette et al. | |
| 2011/0097381 | A1 | 4/2011 | Binette et al. | |
| 2011/0110958 | A1 * | 5/2011 | Qiu et al. | 424/174.1 |
| 2011/0177134 | A1 * | 7/2011 | Harmon et al. | 424/400 |
| 2012/0156265 | A1 | 6/2012 | Binette et al. | |
| 2012/0165939 | A1 | 6/2012 | Kladakis et al. | |
| 2012/0253464 | A1 | 10/2012 | Hwang et al. | |

FOREIGN PATENT DOCUMENTS

| | | |
|---|---|---|
| DE | 198 12 195 | 9/1999 |
| EP | 0 145 492 | 6/1985 |
| EP | 0 274 898 | 7/1988 |
| EP | 0 277 678 | 8/1988 |
| EP | 0 464 163 | 6/1991 |
| EP | 0 562 864 | 3/1993 |
| EP | 0 955 024 | 11/1999 |
| EP | 1 027 897 | 8/2000 |
| EP | 1 064 958 | 1/2001 |
| EP | 1 167 517 | 1/2002 |
| EP | 1 177 800 | 2/2002 |
| EP | 1 216 718 | 6/2002 |
| EP | 1 348 451 | 10/2003 |
| EP | 1 405 649 | 4/2004 |
| EP | 1 410 811 | 4/2004 |
| EP | 1 506 790 | 2/2005 |
| EP | 1 537 839 | 6/2005 |
| EP | 1 604 622 | 12/2005 |
| FR | 2688690 | 9/1993 |
| GB | 1008193 | 10/1965 |
| JP | 63-203154 | 8/1988 |
| JP | 63-203154 A | 8/1988 |
| JP | 02-052648 | 2/1990 |
| JP | 2143945 | 6/1990 |
| JP | 19900227442 | 4/1992 |
| JP | 19900256824 | 5/1992 |
| JP | 19910261753 | 7/1993 |
| JP | 19920094329 | 11/1993 |
| JP | 10234844 | 9/1998 |
| JP | 11-319068 A | 11/1999 |
| JP | 19980129048 | 11/1999 |
| JP | 19980319783 | 5/2000 |
| JP | 2001129073 | 5/2001 |
| JP | 2002-527402 A | 8/2002 |

(56) References Cited

FOREIGN PATENT DOCUMENTS

| | | | |
|---|---|---|---|
| JP | 2002-535378 A | 10/2002 |
| JP | 2003320008 | 11/2003 |
| JP | 2004008437 | 1/2004 |
| JP | 20020165345 | 1/2004 |
| JP | 2004-195103 | 7/2004 |
| JP | 2005-237476 A | 9/2005 |
| RU | 2187261 | 8/2002 |
| SU | 1535542 | 1/1990 |
| WO | WO 86/00533 | 1/1986 |
| WO | WO 92/06179 | 4/1992 |
| WO | WO 93/02718 | 2/1993 |
| WO | WO 93/11805 | 6/1993 |
| WO | WO 95/33821 | 12/1995 |
| WO | WO 96/08277 | 3/1996 |
| WO | WO 97/30662 | 8/1997 |
| WO | WO 97/46665 | 12/1997 |
| WO | WO 98/48860 | 11/1998 |
| WO | WO 98/53768 | 12/1998 |
| WO | WO 99/05992 | 2/1999 |
| WO | WO 99/16381 | 4/1999 |
| WO | WO 99/39724 | 8/1999 |
| WO | WO 99/47097 | 9/1999 |
| WO | WO 99/59647 | 11/1999 |
| WO | WO 00/15248 | 3/2000 |
| WO | WO 00/16381 | 3/2000 |
| WO | WO 00/69355 | 11/2000 |
| WO | WO 00/72782 | 12/2000 |
| WO | WO 00/74741 | 12/2000 |
| WO | WO 01/15753 | 3/2001 |
| WO | WO 01/34065 | 5/2001 |
| WO | WO 01/85226 | 11/2001 |
| WO | WO 02/00272 | 1/2002 |
| WO | WO 02/05750 | 1/2002 |
| WO | WO 02/30324 | 4/2002 |
| WO | WO 02/062357 | 8/2002 |
| WO | WO 02/074356 | 9/2002 |
| WO | WO 02/096268 | 12/2002 |
| WO | 03/007784 A2 | 1/2003 |
| WO | 03/007786 A2 | 1/2003 |
| WO | 03/007787 A2 | 1/2003 |
| WO | 03/007788 A2 | 1/2003 |
| WO | 03/007790 A2 | 1/2003 |
| WO | 03/007805 A2 | 1/2003 |
| WO | 03/007839 A2 | 1/2003 |
| WO | 03/007847 A1 | 1/2003 |
| WO | WO 03/007789 | 1/2003 |
| WO | WO 03/017826 | 3/2003 |
| WO | WO 03/043674 | 5/2003 |
| WO | WO 2004/012782 | 2/2004 |

OTHER PUBLICATIONS

Albrecht. F.H., "The Closure of Joint Cartilage Defects by Means of Cartilage Fragments and Fibrin Adhesive," Fortschr. Med. 101(37):1650-52 (1983).

Allcock in *The Encyclopedia of Polymer Science*, vol. 13, pp. 31-41, Wiley Intersciences, John Wiley & Sons, 1988.

Australian Search Report for AU application No. 2006200194, mailed Feb. 4, 2008.

Boland et. al., J. Macromol. Sci.—Pure Appl. Chem., 2001, A38(12), p. 1231-1243.

Bonisch, M et al. "Septumredonstrucktion mit PDS-Folie" HNO 47: 1999 pp. 546-550.

Buschmann et al., J. Orthop. Res. 1992; 10:745-752.

Caterson EJ., et al. "Three-Dimensional Cartilage Formation by Bone Marrow-Derived Cells Seeded in Polylactide/Alginate Amalgam," *J Biomed Mater Res*. 57(3):394-403 (2001).

Chen G., Ushida T. and Tateishi T. "A hybrid network of synthetic polymer mesh and collagen sponge," Chem. Commun., 2000, 1505-1506.

De Groot, J.H. et al., "Meniscal tissue regeneration in porous 50/50 copoly(I-lactide/epsilon-caprolactone) implants" Biomaterials, vol. 18, No. 8, 1997, pp. 613-622.

De Groot, J.H. et al., "Use of porous polyurethanes for meniscal reconstruction and meniscal prostheses" Biomaterials, vol. 17, No. 2, 1996, pp. 163-173.

Defrere et al., "Teflon/polyurethane arthroplasty of the knee: the first 2 years preliminary clinical experience in a new concept of artificial resurfacing of full thickness cartilage legions of the knee," Acta Chir. Belg., 1992, vol. 92, No. 5, pp. 217-227.

Deuel, T. et al., "Growth Factors in Principles of Tissue Engineering," Second Edition, Academic Press pp. 129-141 (2000).

Dialog English language abstract for DE 19812195, published Sep. 30, 1999.

Eckersberger, M.D., Franz, "Circumferential tracheal replacement with costal cartilage", The Journal of Thoracic and Cardiovascular Surgery, 1987;94: pp. 175-180.

European Search Report for EP 08075114.2, mailed May 12, 2010.

European Search Report for EP 10075307 mailed Oct. 6, 2010.

European Search Report, for EP 03 25 6522, mailed Feb. 24, 2004.

European Search Report, for EP Application No. 07252617.1, mailed Nov. 2, 2007.

Examination file history of EP 01310810, priority date of Dec. 21, 2000.

Frenkel, S, Ph.D. and Paul E. Di Cesare, M.D., "Degradation and Repair of Articular Cartilage," *Frontiers in Bioscience*, $4^{th}$ ed., pp. 671-685, pp. 1-32 (Oct. 15, 1999).

Gooch, K. et al., "Mechanical Forces and Growth Factors Utilized in Tissue Engineering" Frontier in Tissue Engineering, *Pergamon* Chapter II.3, pp. 61-82 (1998).

Grigolo, B., et al. "Transplantation of Chondrocytes Seeded on a Hyaluronan Derivative (hyaff-11) into Cartilage Defects in Rabbits," *Biomaterials* 22(17):2417-2424 (2001).

Heller: 'Handbook of Biodegradable Polymers', 1997, Hardwood Academic Press pp. 99-118.

Hutmacher DW., "Scaffold Design and Fabrication Technologies for Engineering Tissues—State of the Art and Future Prospectives", *J Biomater Sci Polym Ed*, 12(1):107-124 (2001).

Hutmacher DW., "Scaffolds in Tissue Engineering Bone and Cartilage", *Biomaterials*, 21(24):2529-2543 (2000).

Ibarra, C. M.D. et al. "Tissue-Engineered Meniscus—Cells and Matrix", *Tissue Engineering in Orthopedic Surgery* 31(3):411-418 (Jul. 2000).

Ikeda, Yoshito, Handbook of Fiber Science and Technology, Edited by Menachem Lewin, Jack Preston, vol. III, Part B, Chapter 8, pp. 253, 289-295, Published by M. Dekker, 1983.

Journal of Biomaterials Research, vol. 22, pp. 993-1009, 1988 by Cohn and Younes.

Kemnitzer and Kohn, in the *Handbook of Biodegradable Polymers*, edited by Domb, et. al., Hardwood Academic Press, pp. 251-272 (1997).

Koski, J. M.D. et al., "Meniscal Injury and Repair", *Orthopedic Clinics of North American*, 31(3):419-435 (Jul. 2000).

Koski, J. M.D. et al., "Tissue-Engineered Ligament—Cells, Matrix, and Growth Factors" *Tissue Engineering in Orthopedic Surgery*, 31(3):437-452 (Jul. 2000).

Kurashina, K. et al. "Osteogenesis in muscle with composite graft of hydroxyapatite and autogenous calvarial periosteum: a preliminary report" Biomaterials (1995) vol. 16, No. 2, pp. 119-123.

Matsuo, M.D., Kiyoshi et al., "Semiquantitative Correction of Posttraumatic Enophthalmos with Sliced Cartilage Grafts" Plastic and Reconstructive Surgery, vol. 83, No. 3, Postraumatic Enophthalmos, pp. 429-437 (1989).

Megumi, M.D., Yoshikazu, "Augmentation Rhinoplasty with Soft Tissue and Cartilage" Aesthetic Plastic Surgery, 1988, pp. 89-93.

Microcellular Foams via Phase Separation, J. Vac. Sci. Technolol., A.T. Young, vol. 4(3), May/Jun. 1986.

Murray, M., et al. "The Migration of Cells from the Ruptured Human Anterior Cruciate Ligament into Collagen-Glycosaminoglycan Regeneration Templates in Vitro," *Biomaterials* 22:2393-2402 (2001).

Nioshiki Y., "A new trend in hybrid artificial organs" J. Artificial Organs, 1999, vol. 2: pp. 93-96.

Papadopulos, M.D., Angel, "Compound Implant to Project the Nasal Tip" Aesthetic Plastic Surgery, 1987, pp. 181-185.

(56) References Cited

OTHER PUBLICATIONS

Partial European Search Report, for EP 04 25 7515, mailed May 9, 2005.
Polymer Preprints (ACS Division of Polymer Chemistry), vol. 30(1), p. 498, 1989 by Cohn.
Powers, Dennis L. et al., "A cartilagenous graft as an adjunct to finger joint implant arthroplasty" Journal of Biomedical Materials Research, vol. 19, 1985 pp. 509-518.
Radice, M. "Hyaluronan-Based Biopolymers as delivery vehicles for Bone-Marrow-Derived Mesenchymal Progenitors", *J Biomed Mater Res*. 50(2):101-9 (2000).
Rohrbach, Jens Martin et al., "Biological Corneal Replacement—Alternative to Keratoplasty and Keratoprosthesis? A Pilot Study with Heterologous Hyaline Cartilage in the Rabbit Model", Klin Monatsbl Augenheilkd 207, 1995; pp. 191-196.
Rossi, et al., "Embryonic Purkinje Cells Grafted on the Surface of the Cerebellar Cortex Integrate in the Adult Unlesioned Cerebellum," EP J. Neuroscience 4:589-93 (1992).
Sampath, T. K., et al. "In Vitro Transformation of Mesenchymal Cells Derived From Embryonic Muscle Into Cartilage in Response to Extracellular Matrix Components of Bone," *Proceedings of the National Academy of Science of the USA*, 81(1): 3419-3423 (Jun. 1984).
Schreiber RE., et al. "A Method for Tissue Engineering of cartilage by Cell Seeding on Bioresorbable Scaffolds," *Ann NY Acad Sci*. 875:394-404 (1999).
Solov'ev et al., "Functional Activity of Hepatocytes in Liver Fragments In Vitro as a Function if Fragment Size and Duration of Culturing" Bull Exp Biol Med. Jun. 2000;129(6):595-7.
Spaans et al. "Solvent-free fabrication of micro-porous polyurethane amide and polyurethane-urea scaffolds for repair and replacement of the knee joint meniscus" Journal of Biomaterials, vol. 21, No. 23, 2000, pp. 2453-2460.
Stone, K. et al. "Meniscal Regeneration with Copolymeric Collagen Scaffolds," *American Journal of Sports Medicine* 20(2):104-111 (1992).
Tienen T. G. et al., "A porous polymer scaffold for meniscal lesion repair—A study in dogs" Biomaterials, vol. 24, No. 14, 2003, pp. 2541-2548.
Tozum et al., J Canadian Dental Assoc. Nov. 2003 69(10):664-664h.
Trenite, M.D., G.J. Nolst et al.., "Reimplantation of autologous septal cartilage in the growing nasal septum", Rhinology, 25, 1987, pp. 225-236.
van Susante JLC, et al. "Linkage of Chondroitin-Sulfate to Type I Collagen Scaffolds Stimulates the Bioactivity of Seeded Chondrocytes in Vitro", *Biomaterials* 22(17):2359-2369 (2001).
Vandorpe, et al in the *Handbook of Biodegradable Polymers*, edited by Domb, et al., Hardwood Academic Press, pp. 161-182 (1997).
www.bio-medicine.org/medicine-technology-1/New-Study-Shows-Cloning-From-Dried-Cells-Now-Possible-2988-1/, 2 pgs, printed Jan. 11, 2010.
www.btc-bti.com/applications/cryogenicstorage.htm, 6 pgs, printed Jan. 11, 2010.
Andreasen, J.O. et al. Evaluation of different types of autotransplanted connective tissues as potential periodontal ligamant substitues: An experimental replantation study in monkeys, International Journal of Oral Surgery, Jun. 1981, vol. 10, Issue 3, pp. 189-201 (Abstract only).
Japanese Office Action, from JP 2004-191861, mailed Mar. 1, 2011.
Japanese Office Action issued Dec. 6, 2011 for Application No. 2004-233655 (8 Pages).
Andreasen et al., Evaluation of different types of autotransplanted connective tissues as potential periodontal ligamant substitues: An experimental replantation study in monkeys, International Journal of Oral Surgery, Jun. 1981, vol. 10, Issue 3, pp. 189-201.
Japanese Office Action issued Feb. 26, 2013 for Application No. 2007-171032 (4 pages).
Takeuchi et al., Journal of Clinical and Experimental Medicine. 1995, vol. 175(10), p. 748-9 (English translation).
[No Author Listed] Journal of Clinical and Experimental Medicine. 1995, vol. 175(10), p. 748-9.
European Search Report issued Mar. 28, 2002 for Application No. 01310810.5 (3 pages).
Japanese Office Action issued Aug. 28, 2012 for Application No. 2004-233655 (6 pages).
Japanese Office Action issued Apr. 24, 2012 for Application No. 2007-171032 (6 pages).

* cited by examiner

FIG. 6A
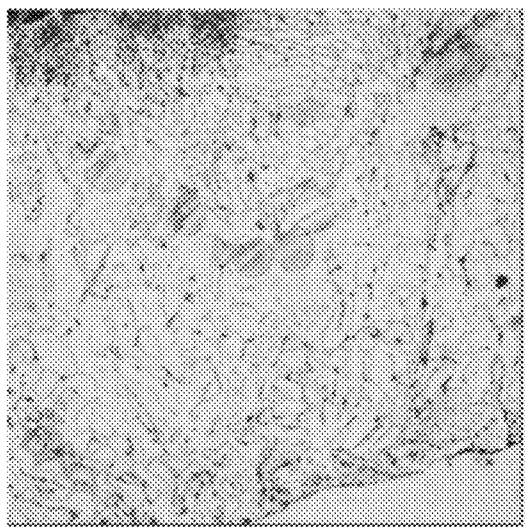
FIG. 6B
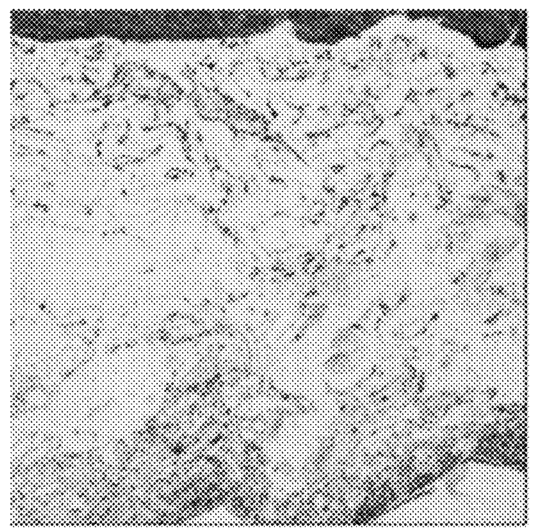
FIG. 6C

VIABLE TISSUE REPAIR IMPLANTS AND METHODS OF USE

CROSS REFERENCE TO RELATED APPLICATIONS

This application is a continuation of U.S. Ser. No. 10/729,046 filed on Dec. 5, 2003 and entitled "Viable Tissue Repair Implants and Methods of Use," which is hereby incorporated by reference in its entirety.

STATEMENT REGARDING FEDERALLY SPONSORED RESEARCH

Not applicable.

FIELD OF THE INVENTION

The present invention relates to methods and apparatus for the treatment of tissue injuries or defects. Specifically, the present invention relates to tissue repair and augmentation implants, and more particularly, to tissue implants having viable cells capable of tissue regeneration and integration with tissue surrounding the area to be repaired, as well as methods for using such tissue implants.

BACKGROUND OF THE INVENTION

Injuries to tissue, such as cartilage, skin, muscle, bone, tendon, and ligament where the tissue has been injured or traumatized frequently require surgical intervention to repair the damage and facilitate healing. Such surgical repairs can include suturing or otherwise repairing the damaged tissue with known medical devices, augmenting the damaged tissue with other tissue, using an implant, a graft or any combination of these techniques. Despite these conventional methods of tissue repair, there continues to be a need for surgical solutions that facilitate the regeneration of new, healthy tissue to provide more reliable repair and heating of the injured or damaged tissue over the long term.

The search for a reliable source of viable cells for tissue regeneration has been pursued for years. Recent tissue engineering techniques for repairing tissue have typically involved replacing or reconstructing damaged or injured tissue with cells that have been manipulated ex vivo to stimulate new tissue growth. The cells are usually incorporated into a delivery vehicle (e.g., a scaffold or surgical implant) for placement at the tissue site, whereupon new tissue can be grown. Various surgical implants are known and have been used in surgical procedures to help achieve these benefits. For example, it is known to use various devices and techniques for creating implants having isolated cells loaded onto a delivery vehicle. Such cell-seeded implants have been used in an in vitro method of making and/or repairing cartilage by growing cartilaginous structures that consist of chondrocytes seeded onto biodegradable, biocompatible fibrous polymeric matrices as well as matrices developed from collagenous materials. Such methods require the initial isolation of chondrocytes from cartilaginous tissue prior to the chondrocytes being seeded onto the polymeric matrices. Other techniques for repairing damaged tissue employ implants having stem or progenitor cells that are used to produce the desired tissue. For example, it is known to use stem or progenitor cells, such as the cells within tatty tissue, muscle, bone marrow, or embryonic tissue to regenerate bone, cartilage, and other soft tissues in a patient. For example, stem cells from fat are removed from the patient and placed in an environment favorable to cartilage formation, thereby inducing the cells to proliferate and to create a different type of cell, such as cartilage cells.

While the trend towards using tissue engineering approaches to tissue repair continues to gain popularity, mainly because of the long-term benefits provided to the patient, these current techniques are not without drawbacks. One disadvantage with current tissue engineering techniques is that they can be time consuming. A typical process involves the harvest of a tissue sample from the patient in a first surgical procedure, which is then transported to a laboratory for cell isolation, culture and amplification. The cell sample is grown for a period of 3 to 4 weeks using standard cell culture techniques to create a cell bank. Once the cell population has reached a target number, the cells are sent back to the surgeon for implantation during a second surgical procedure. This manual, labor-intensive process is extremely costly and time consuming. Although the clinical data suggest long-term benefits for the patient, the prohibitive cost of the procedure, combined with the traumatic impact of two surgical procedures, has hampered adoption of these techniques.

One method for tissue repair has been to place into a defect site an implant that is composed of cultured and amplified cells and a scaffold, which provides structural integrity and a surface area for cell adhesion and proliferation. In the past, such scaffolds have consisted mostly of two- or three-dimensional porous scaffolds that allow cell invasion and remodeling once the scaffold has been combined with living cells and has been delivered inside the patient. This model is limited in application because of the secondary surgery and high costs involved. And though allografts have been used for tissue repair in the past, this solution is also not ideal because of the limited availability of graft material and the potential for disease transmission.

For these reasons, there continues to exist a need in this art for novel devices and methods for regenerating tissue which are less time consuming and easier to implement. It is also desirable to provide an implant which can serve as a reliable source of viable cells, and which can be made in a quick and efficient manner for immediate use during surgery. There is thus a need for a less costly solution to repairing tissue defects or injuries that also provides the advantages of tissue regeneration, without the encumbrances of the currently available devices and methods of tissue repair previously mentioned.

SUMMARY OF THE INVENTION

The present invention provides a biocompatible tissue implant for repairing a tissue defect or injury which comprises a biological tissue slice that serves as a source of viable cells capable of tissue regeneration and/or repair. The biological tissue slice can be harvested from healthy tissue during the tissue repair surgery to have a geometry that is suitable for implantation at the site of the injury or defect. The harvested tissue slice is dimensioned to allow the viable cells contained within the tissue slice to migrate out and proliferate and integrate with tissue surrounding the tissue repair site. The implant can be delivered to the tissue site either alone or with a retaining element to secure the implant to the injury or defect site. In one embodiment, the harvested tissue slice can be combined with minced tissue fragments to further enhance tissue regrowth. The minced tissue fragments can be delivered in a hydrogel or adhesive, which can also function as the retaining element. Optionally, a biologically active agent can be added to the implant at the tissue repair site to further enhance tissue healing or regeneration.

In another embodiment of the present invention, the implant can comprise more than one tissue slice. The plurality of tissue slices can be joined together to form a layered tissue implant having a desired size and geometry suitable for implantation at the injury or defect site. In yet another embodiment, a tissue slice can be joined to a tissue scaffold to form a composite implant. The implant can comprise a plurality of both tissue slices and scaffold layers. The scaffold can further include a biologically active agent that enhances the effectiveness of the viable cells contained within the tissue slice to grow and integrate with the surrounding tissue area.

The present invention also provides a method of treating injured or diseased tissue using the biocompatible tissue implants of the present invention that involves delivering the tissue implant to the site of the tissue injury or defect. The tissue implant can optionally be secured to the tissue site with a retaining element. Once implanted, the viable cells contained within the implant can begin regenerating new tissue to be integrated into the tissue surrounding the repair site. The biocompatible tissue implants of the present invention can be used for the repair and/or regeneration of diseased or damaged tissue. Further, the tissue implants can be used for tissue bulking, cosmetic treatments, therapeutic treatments, tissue augmentation, and tissue remodeling. In embodiments in which the implant is used for tissue repair, the tissue repair implant can be used to treat a variety of injuries, such as for example, injuries occurring within the musculoskeletal system, such as rotator cuff injuries, anterior cruciate ligament (ACL) ruptures, or meniscal tears, as well as injuries occurring in other connective tissues, such as skin and cartilage. Furthermore, such implants can be used in other orthopaedic surgical procedures, such as hand and foot surgery, to repair tissues such as ligaments, nerves, and tendons.

By harvesting the tissue slice from viable, healthy tissue during the tissue repair surgery, the present invention provides a cell source for repairing the tissue injury or defect at minimal cost and without the need for additional surgeries. This method allows for the delivery of viable cells to an injury or defect site without the cost of cell isolation and amplification. Further, because the present invention does not require the tissue slice to be minced to fine particles, manipulation time is reduced and the viability of the cells within the tissue is improved. An additional advantage of using a tissue slice as a cell source for viable, healthy cells is that the tissue slice can provide a native tissue surface for the biocompatible tissue implant, which will then have similar mechanical properties to that of neighboring tissue. The tissue slice also provides a structure for better retention of the cells at the injury or defect site that can be easily fixed to the site using conventional methods such as sutures, staples, or glues. In addition, by using a thin tissue slice, the cells have the ability to migrate out from the tissue and provide good integration between the implanted tissue and the injury or defect site.

BRIEF DESCRIPTION OF THE DRAWINGS

The invention can be more fully understood from the following detailed description taken in conjunction with the accompanying exemplary drawing, in which:

FIGS. 6A-6C are photomicrographs of histological sections of samples obtained after 3 weeks following the procedure of EXAMPLE 2, demonstrating cell migration from a meniscal tissue sample into a polymer scaffold;

DETAILED DESCRIPTION OF THE INVENTION

Figure 1A:
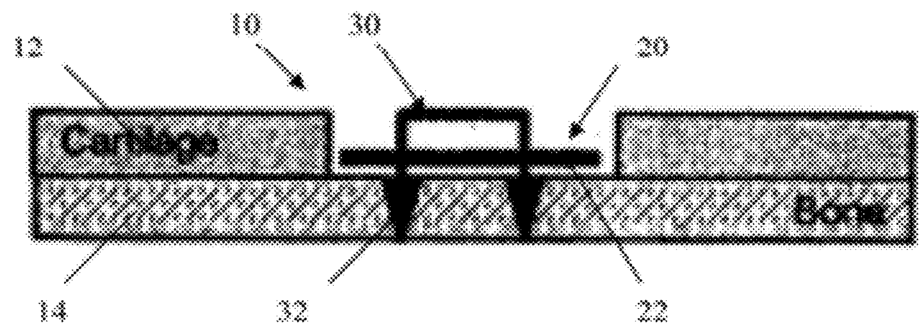
FIG. 1A illustrates an exemplary embodiment of the tissue implant secured to a tissue defect with a retaining element of the present invention.

The biocompatible tissue implants of the present invention are used in the treatment of various types of tissue for various purposes. For example, the implants can be used for the repair and/or regeneration of diseased or damaged tissue, or they can be used for tissue bulking, tissue augmentation, cosmetic treatments, therapeutic treatments, and for tissue sealing. The tissue implants include a tissue slice or strip harvested from healthy tissue that contains viable cells capable of tissue regeneration and/or remodeling. The tissue slice is harvested to have a geometry that is suitable for implantation at the site of the injury or defect. The harvested tissue slice is dimensioned to allow the viable cells contained within the tissue slice to migrate out and proliferate and integrate with tissue surrounding the repair site.

Although the implants are sometimes referred to herein as "tissue repair implants" and the methods of using the implants are sometimes characterized as tissue repair techniques, it is understood that the implants can be used for a variety of tissue treatments, including but not limited to tissue repair, tissue bulking, cosmetic treatments, therapeutic treatments, tissue remodeling or augmentation, and tissue sealing.

The term "viable," as used herein, refers to a tissue sample having one or more viable cells. Virtually any type of tissue can be used to construct the tissue repair implants of the present invention. Preferably, the tissue used is selected from cartilage tissue, meniscal tissue, ligament tissue, tendon tissue, skin tissue, bone tissue, muscle tissue, periosteal tissue, pericardial tissue, synovial tissue, nerve tissue, fat tissue, kidney tissue, bone marrow, liver tissue, bladder tissue, pancreas tissue, spleen tissue, intervertebral disc tissue, embryonic tissue, periodontal tissue, vascular tissue, blood and combinations thereof. In one embodiment useful for cartilage repair, the tissue is free of bone tissue and is selected from the group consisting of cartilage tissue, meniscal tissue, periosteal tissue, fat tissue, bone marrow, blood, synovial tissue, ligament tissue and tendon tissue. The tissue used to construct the tissue implant can be autogeneic tissue, allogeneic tissue, or xenogeneic tissue.

The term "slice," as used herein, refers to a thin section, strip or sliver derived from any of the tissue types described above and used to construct the tissue implant. Preferably, the tissue slice has a thickness less than about 1 mm, and more preferably has a thickness in the range of about 200 μm to about 500 μm. A thin profile ensures proper migration of the cells out of the tissue slice. It is understood, however, that the tissue slice can have any length or width appropriate for implantation at the defect, since these parameters do not greatly affect cell migration out of the tissue slice.

In one aspect of the invention, the tissue slices can be combined with finely minced tissue fragments to enhance the effectiveness of the regrowth and healing response. In such an embodiment, the tissue slices can be as thick as about 3 mm. However, the tissue slices are preferably between about 200 μm to about 1 mm.

In another aspect of the invention, the sliced tissue may be contacted with a matrix-digesting enzyme to facilitate cell migration out of the extracellular matrix surrounding the cells. The enzymes can be used to increase the rate of cell migration out of the extracellular matrix and into the tissue defect or injury, or scaffold material. Suitable matrix-digesting enzymes that can be used in the present invention include, but are not limited to, collagenase, chondroitinase, trypsin, elastase, hyaluronidase, peptidase, thermolysin, matrix metalloproteinase, gelatinase and protease.

In one embodiment useful for meniscal repair, the tissue used in the tissue repair implant can be selected from the group consisting of meniscal tissue, cartilage tissue, skin, synovial tissue, periosteal tissue, pericardial tissue, fat tissue, bone marrow, blood, tendon tissue, ligament tissue, or combinations thereof. In one embodiment useful for ligament repair, the tissue used in the tissue repair implant can be selected from the group consisting of tendon tissue, ligament tissue of the same type that is to be repaired, ligament tissue of a different type than the tissue that is to be repaired, synovial tissue, periosteal tissue, fascia, skin, and combinations thereof.

Turning now to the drawings and particularly to FIG. 1A, an exemplary embodiment of the biocompatible tissue implant 20 of the present invention is shown. In the illustrated example, the tissue implant 20 is used to repair a cartilage defect 10. The tissue implant 20 comprises a tissue slice 22 that has been harvested from healthy, viable cartilage tissue to have a geometry that is suitable for implantation at the defect 10. The tissue slice 22 serves as a source of viable cartilage cells for repairing the cartilage defect, and is dimensioned to allow the viable cells contained within the tissue slice 22 to migrate out and proliferate and integrate with the cartilage tissue 12 surrounding the defect 10. To ensure proper migration of the cells out of the tissue implant 20, the tissue slice 22 has a thickness less than about 1 mm. Preferably, the tissue slice 22 has a thickness in the range of about 200 μm to about 500 μm, and can have any length or width appropriate for implantation at the defect 10.

Figure 1B:
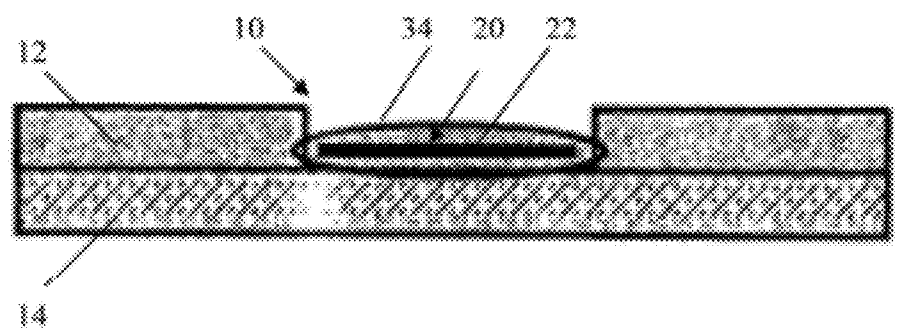
FIG. 1B illustrates the tissue implant of FIG. 1A secured to a tissue defect with another retaining element of the present invention.
Figure 1C:
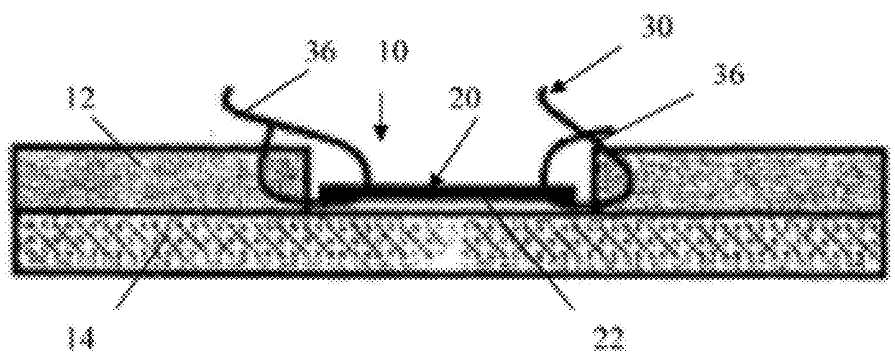
FIG. 1C illustrates the tissue implant of FIG. 1A secured to a tissue defect with yet another retaining element of the present invention.

The tissue implant 20 can be delivered to the cartilage defect 10 and retained at the site of implantation by the force of compression against the tissue implant 20 by the surrounding cartilage tissue 12. For instance, the tissue implant 20 can be dimensioned to have a slightly larger overall size than the area of the defect so that, upon implantation, the tissue implant 20 can form a tight, interference fit within the defect 10. Alternatively, as illustrated in FIGS. 1A through 1C, the tissue implant 20 can be secured using any conventional method such as with a retaining element 30 to fix the tissue implant 20 to the defect 10. The retaining element 30 can comprise a fastener, staple, tissue tack, suture, adhesive, or any combination of these. One skilled in the art will appreciate that the retaining element 30 is not limited, however, to such examples, and can comprise other suitable tissue attachment devices known in the art. Further, a number of factors can determine which retaining element 30 is selected, including the size of the defect, the type of tissue being repaired, and the availability and cost of the retaining element 30.

FIG. 1A illustrates the tissue implant 20 secured in place with a staple 32 which anchors to bone tissue 14 around the cartilage defect 10. The tissue implant 20 can also be secured in place with an adhesive 34 as shown in FIG. 1B. Suitable adhesives 34 include, but are not limited to, hyaluronic acid, fibrin glue, fibrin clot, collagen gel, collagen-based adhesive, alginate gel, crosslinked alginate, gelatin-resorcin-formalin-based adhesive, mussel-based adhesive, dihydroxyphenylalanine (DOPA)-based adhesive, chitosan, transglutaminase, poly(amino acid)-based adhesive, cellulose-based adhesive, polysaccharide-based adhesive, synthetic acrylate-based adhesives, platelet rich plasma (PRP), platelet poor plasma (PPP), PRP clot, PPP clot, blood, blood clot, blood component, blood component clot, polyethylene glycol-based adhesive, Matrigel, Monostearoyl Glycerol co-Succinate (MGSA), Monostearoyl Glycerol co-Succinate/polyethylene glycol (MGSA/PEG) copolymers, laminin, elastin, proteoglycans, and combinations thereof. As shown in FIG. 1C, the tissue implant 20 can also be fixed in place using sutures 36.

The tissue implant 20 can also be used in conjunction with minced tissue to enhance tissue repair. For example, minced tissue fragments can be added to the adhesive 34 to further improve the tissue regeneration and/or remodeling process. Alternatively, the minced tissue fragments can be delivered in a gel-like carrier which is applied to the tissue implant 20 at the defect 10. The minced tissue fragments can fill in the spaces between the tissue slice 22 and the defect 10. In such an embodiment in which minced tissue fragments are combined with the tissue slice, the thickness of the tissue slice forming the tissue implant 20 can be about 3 mm, but preferably is between about 200 μm and about 1 mm. By way of non-limiting example, the gel-like carrier can be a biological or synthetic hydrogel such as hyaluronic acid, fibrin glue, fibrin clot, collagen gel, collagen-based adhesive, alginate gel, crosslinked alginate, chitosan, synthetic acrylate-based gels, platelet rich plasma (PRP), platelet poor plasma (PPP), PRP clot, PPP clot, blood, blood clot, blood component, blood component clot, Matrigel, agarose, chitin, chitosan, polysaccharides, poly(oxyalkylene), a copolymer of poly (ethylene oxide)-poly(propylene oxide), poly(vinyl alcohol), laminin, elasti, proteoglycans, solubilized basement membrane, or combinations thereof.

The minced tissue fragments can be obtained using any of a variety of conventional techniques, such as for example, by biopsy or other surgical removal. Preferably, the tissue sample is obtained during the repair surgery to minimize the total number of surgeries performed on the patient. Once a sample of living tissue has been obtained, the sample can then be processed under sterile conditions to create a suspension having at least one minced, or finely divided, tissue particle. It is also possible to harvest the tissue in minced form such that further processing is not necessary. The particle size of each tissue fragment can vary, for example, the tissue size can be in the range of about 0.1 and 3 $mm^3$, in the range of about 0.5 and 1 $mm^3$, in the range of about 1 to 2 $mm^3$, or in the range of about 2 to 3 $mm^3$, but preferably the tissue particle is less than 1 $mm^3$.

Preferably, the minced tissue has at least one viable cell that can migrate from the tissue fragment. More preferably, the tissue contains an effective amount of cells that can migrate from the tissue fragment and begin populating the tissue surrounding the defect 10. In an optional embodiment, the minced tissue fragments may be contacted with a matrix-digesting enzyme to facilitate cell migration out of the extracellular matrix surrounding the cells. The enzymes are used to increase the rate of cell migration out of the extracellular matrix and into the scaffold material. Suitable matrix-digesting enzymes that can be used in the present invention include, but are not limited to, collagenase, chondroitinase, trypsin, elastase, hyaluronidase, peptidase, thermolysin, matrix metalloproteinase, gelatinase and protease. Preferably, the concentration of minced tissue particles in the gel-carrier is in the range of approximately 1 to 1000 $mg/cm^3$, and more preferably in the range of about 1 to 200 $mg/cm^3$.

Figure 2A:
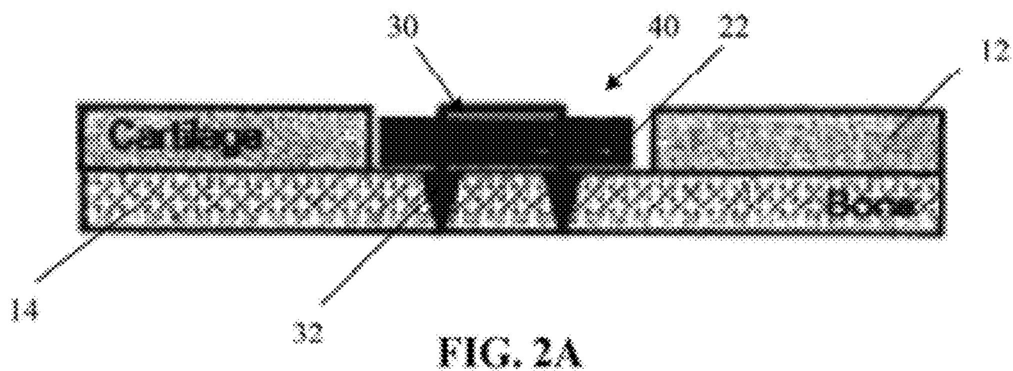
FIG. 2A illustrates another exemplary embodiment of the tissue implant secured to a tissue defect with a retaining element of the present invention.
Figure 2B:
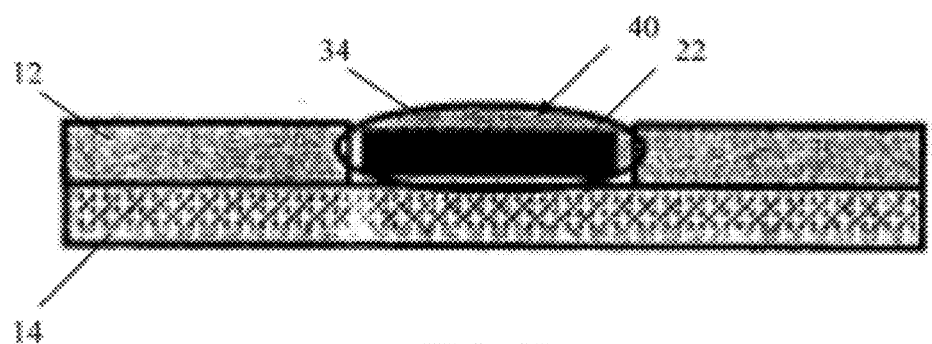
FIG. 2B illustrates the tissue implant of FIG. 2A secured to a tissue defect with another retaining element of the present invention.
Figure 2C:
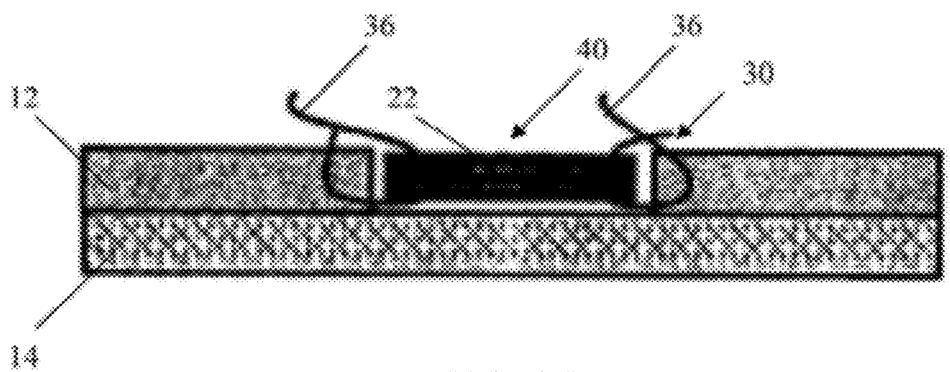
FIG. 2C illustrates the tissue implant of FIG. 2A secured to a tissue defect with yet another retaining element of the present invention.

While it is understood that a single tissue slice 22 is sufficient to form the tissue implant 20 of the present invention, the same principles of cell migration and integration also apply to a layered tissue implant 40 comprising a plurality of tissue slices 22. As illustrated in FIGS. 2A through 2C, a plurality of tissue slices 22 can be joined together to form a layered tissue implant 40 of the present invention. The term "joined," as used herein, broadly refers to the process of combining tissue slices together, such as by the placement of a layer of tissue onto another layer of tissue, either alone or with an additional retaining or adhesive element. Each of the tissue slices 22 can be uniformly sized, or they can be differently sized to form a layered implant 40 having an overall geometry and dimensions suitable for implantation at the site of injury 10. Likewise, the number of tissue slices 22 to be joined together also depends upon the size of the defect, and the size of each of the slices 22. However, to ensure proper migration of the cells out of the tissue implant 40, each of the tissue slice 22 should have a thickness less than about 1 mm as previously described. Preferably, each of the tissue slices 22 has a thickness in the range of about 200 μm to about 500 μm.

Similar to the tissue implant 20 described above, the layered implant 40 can be placed at the tissue defect 10 either alone, or with a retaining element 30 as previously mentioned. In FIG. 2A, the tissue implant 40 is secured to a cartilage defect 10 using a staple 32 that anchors the implant 40 to bone tissue 14 near the defect 10. In FIG. 2B, the tissue implant 40 is held in place with a adhesive 34 such as the ones listed above. To further enhance tissue regeneration and/or remodeling, minced tissue fragments can be mixed in with the adhesive. In such an embodiment in which minced tissue fragments are combined with the tissue slices, the thickness of each tissue slice forming the layered implant 40 can be about 3 mm, but preferably is between about 200 μm and about 1 mm. Finally, the tissue implant 40 can be secured to the cartilage tissue 12 surrounding the defect 10 with sutures 36. After the layered tissue implant 40 has been delivered to the defect 10, tissue regrowth can be further enhanced by applying minced tissue fragments in a gel-like carrier to the tissue implant 40 to fill in the spaces between the tissue slices 22.

Figure 3A:
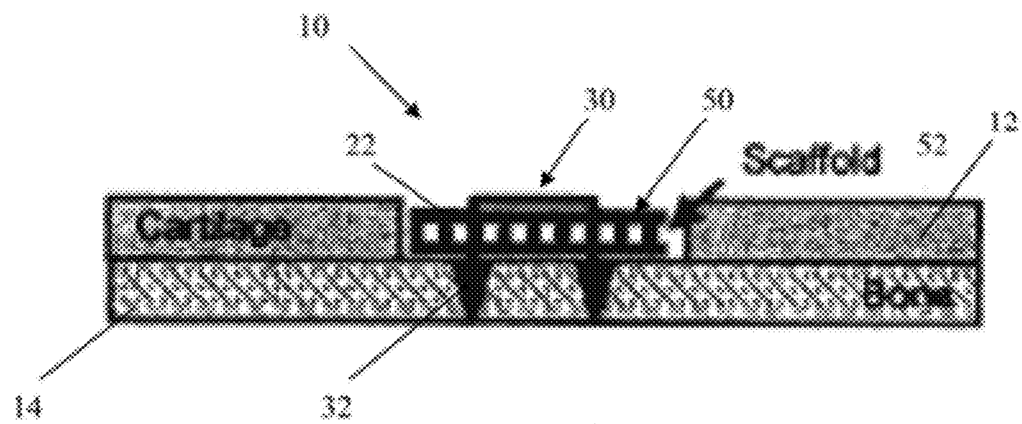
FIG. 3A illustrates yet another exemplary embodiment of the tissue implant secured to a tissue defect with a retaining element of the present invention.
Figure 3B:
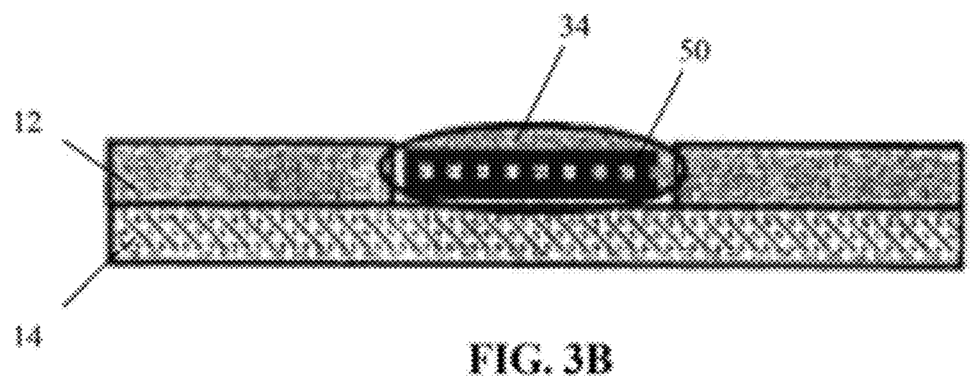
FIG. 3B illustrates the tissue implant of FIG. 3A secured to a tissue defect with another retaining element of the present invention.
Figure 3C:
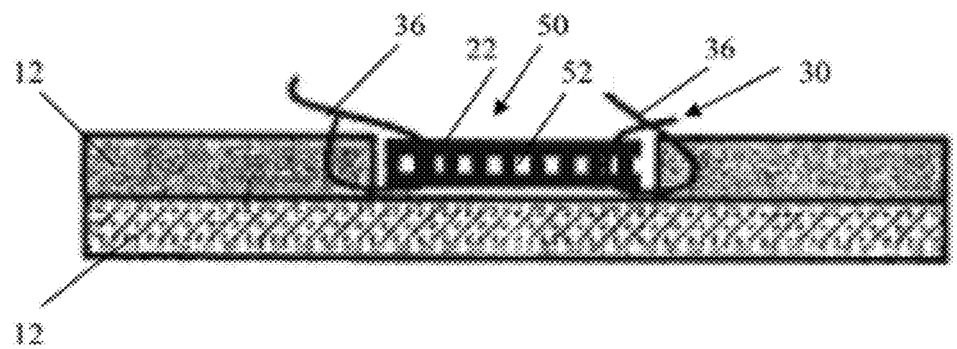
FIG. 3C illustrates the tissue implant of FIG. 3A secured to a tissue defect with yet another retaining element of the present invention.

In yet another embodiment of the present invention, the tissue slice 22 can be combined with a tissue scaffold 52 to form a composite tissue implant 50 as illustrated in FIGS. 3A through 3C. For example, the tissue slice 22 can be placed on the tissue scaffold 52 and delivered to the defect 10 as a composite implant 50. The composite tissue implant 50 can be secured to the cartilage defect 10 using a retaining element 30 such as a staple 32 as shown in FIG. 3A. Alternatively, as illustrated in FIG. 3B the composite tissue implant 50 can be fixed in place using an adhesive 34 such as the ones described above, or using sutures 36 as shown in FIG. 3C. To further enhance tissue regeneration and/or remodeling, minced tissue fragments can be mixed in with the adhesive. In addition, minced tissue fragments in a gel-like carrier can be applied to fill the spaces between the tissue slice 22, tissue scaffold 52, and the defect 10 to enhance tissue growth.

Although illustrated as having a single tissue slice 22 and a single tissue scaffold 52, it is envisioned that the composite tissue implant 50 of the present invention can include a plurality of layers of either tissue slices 22 or tissue scaffolds 52. For instance, in one embodiment a plurality of tissue slices 22 can be sandwiched between layers of the tissue scaffold 52 to form a multilayered, composite implant 50. In another embodiment, the tissue slices 22 and tissue scaffolds 52 can be alternately layered onto one another to form the multilayered, composite implant 50. One skilled in the art will recognize that the number and orientation of tissue slices 22 and scaffolds 52 in the composite implant 50 can vary depending on the size of the defect 10, the type of tissue to be repaired, and the availability of the materials.

Figure 4A:
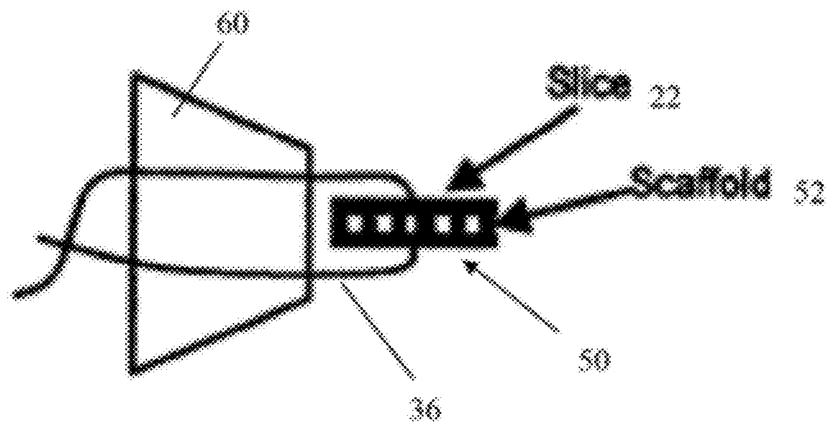
FIG. 4A illustrates the tissue implant of FIG. 3A secured to another tissue defect.
Figure 4B:
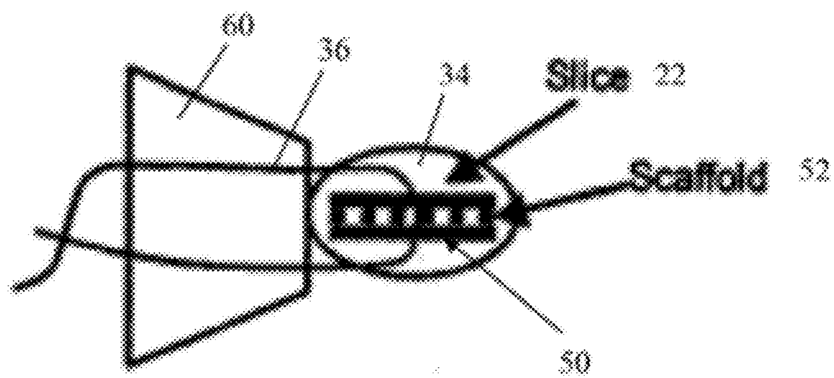
FIG. 4B illustrates the tissue implant of FIG. 4A with an additional retaining element.

With the present embodiment, the tissue scaffold 52 can offer several advantages to the composite implant 50. A tissue scaffold 52 provides additional structural integrity for cellular growth to occur. The tissue scaffold 52 also provides structural support for the tissue slice 22 itself, which can be necessary to help retain the implant 50 in place for certain tissue repairs. For example, in a partial meniscal replacement shown in FIG. 4A, the tissue scaffold 52 provides additional strength to the tissue slice 22 of the composite tissue implant 50 so that the implant 50 can be secured by sutures 36 to the meniscal tissue. If necessary or desired, a combination of retaining elements 30 can be used to secure the composite implant 50 to the meniscal tissue 60. As shown in FIG. 4B, the composite implant 50 can be secured using both sutures 36 and an adhesive or glue 34. Another advantage provided by tissue scaffolds is that they can act as a delivery vehicle for bioactive agents or effectors which enhance the overall effectiveness of the viable cells to grow and integrate with the tissue surrounding the defect 10.

It is contemplated that the tissue scaffold 52 can be formed using virtually any material or delivery vehicle that is biocompatible and that has sufficient structural integrity and physical and/or mechanical properties to effectively provide for ease of handling in an operating room environment. Sufficient strength and physical properties are developed in the scaffold through the selection of materials used to form the scaffold, and the manufacturing process. In some embodiments, the scaffold is also pliable so as to allow the scaffold to adjust to the dimensions of the target site of implantation. For instance, the scaffold can comprise a gel-like material or an adhesive material, as well as a foam or mesh structure. Preferably, the scaffold can be a bioresorbable or bioabsorbable material.

In one embodiment of the present invention, the scaffold can be formed from a biocompatible polymer. A variety of biocompatible polymers can be used to make the biocompatible tissue implants or scaffold devices according to the present invention. The biocompatible polymers can be synthetic polymers, natural polymers or combinations thereof. As used herein the term "synthetic polymer" refers to polymers that are not found in nature, even if the polymers are made from naturally occurring biomaterials. The term "natural polymer" refers to polymers that are naturally occurring. In embodiments where the scaffold includes at least one synthetic polymer, suitable biocompatible synthetic polymers can include polymers selected from the group consisting of aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, poly (propylene fumarate), polyurethane, poly(ester urethane), poly(ether urethane), and blends and copolymers thereof. Suitable synthetic polymers for use in the present invention can also include biosynthetic polymers based on sequences found in collagen, laminin, glycosaminoglycans, elastin, thrombin, fibronectin, starches, poly(amino acid), gelatin, alginate, pectin, fibrin, oxidized cellulose, chitin, chitosan, tropoelastin, hyaluronic acid, silk, ribonucleic acids, deoxyribonucleic acids, polypeptides, proteins, polysaccharides, polynucleotides and combinations thereof.

For the purpose of this invention aliphatic polyesters include, but are not limited to, homopolymers and copolymers of lactide (which includes lactic acid, D-,L- and meso lactide); glycolide (including glycolic acid); ϵ-caprolactone; p-dioxanone (1,4-dioxan-2-one); trimethylene carbonate (1,3-dioxan-2-one); alkyl derivatives of trimethylene carbonate; δ-valerolactone; β-butyrolactone; γ-butyrolactone; ϵ-decalactone; hydroxybutyrate; hydroxyvalerate; 1,4-dioxepan-2-one (including its dimer 1,5,8,12-tetraoxacyclotetradecane-7,14-dione); 1,5-dioxepan-2-one; 6,6-dimethyl-1,4-dioxan-2-one; 2,5-diketomorpholine; pivalolactone; α,α diethylpropiolactone; ethylene carbonate; ethylene oxalate; 3-methyl-1,4-dioxane-2,5-dione; 3,3-diethyl-1,4-dioxan-2,5-dione; 6,6-dimethyl-dioxepan-2-one; 6,8-dioxabicycloctane-7-one and polymer blends thereof. Aliphatic polyesters used in the present invention can be homopolymers or copolymers (random, block, segmented, tapered blocks, graft, triblock, etc.) having a linear, branched or star structure. Other useful polymers include polyphosphazenes, co-, ter- and higher order mixed monomer based polymers made from L-lactide, D,L-lactide, lactic acid, glycolide, glycolic acid, para-dioxanone, trimethylene carbonate and ϵ-caprolactone.

As used herein, the term "glycolide" is understood to include polyglycolic acid. Further, the term "lactide" is understood to include L-lactide, D-lactide, blends thereof, and lactic acid polymers and copolymers.

Elastomeric copolymers are also particularly useful in the present invention. Suitable elastomeric polymers include those with an inherent viscosity in the range of about 1.2 dL/g to 4 dL/g, more preferably about 1.2 dL/g to 2 dL/g and most preferably about 1.4 dL/g to 2 dL/g as determined at 25° C. in a 0.1 gram per deciliter (g/dL) solution of polymer in hexafluoroisopropanol (HFIP). Further, suitable elastomers exhibit a high percent elongation and a low modulus, while possessing good tensile strength and good recovery characteristics. In the preferred embodiments of this invention, the elastomer exhibits a percent elongation greater than about 200 percent and preferably greater than about 500 percent in addition to these elongation and modulus properties, suitable elastomers should also have a tensile strength greater than about 500 psi, preferably greater than about 1,000 psi, and a tear strength of greater than about 50 lbs/inch, preferably greater than about 80 lbs/inch.

Exemplary biocompatible elastomers that can be used in the present invention include, but are not limited to, elastomeric copolymers of ϵ-caprolactone and glycolide with a mole ratio of ϵ-caprolactone to glycolide of from about 35:65 to about 65:35, more preferably from 45:55 to 35:65; elastomeric copolymers of ϵ-caprolactone and lactide (including L-lactide, D-lactide, blends thereof, and lactic acid polymers and copolymers) where the mole ratio of ϵ-caprolactone to lactide is from about 95:5 to about 30:70 and more preferably from 45:55 to 30:70 or from about 95:5 to about 85:15; elastomeric copolymers of p-dioxanone (1,4-dioxan-2-one) and lactide (including L-lactide, D-lactide, blends thereof, and lactic acid polymers and copolymers) where the mole ratio of p-dioxanone to betide is from about 40:60 to about 60:40; elastomeric copolymers of ϵ-caprolactone and p-dioxanone where the mole ratio of ϵ-caprolactone to p-dioxanone is from about from 30:70 to about 70:30; elastomeric copolymers of p-dioxanone and trimethylene carbonate where the mole ratio of p-dioxanone to trimethylene carbonate is from about 30:70 to about 70:30; elastomeric copolymers of trimethylene carbonate and glycolide (including polyglycolic acid) where the mole ratio of trimethylene carbonate to glycolide is from about 30:70 to about 70:30; elastomeric copolymers of trimethylene carbonate and lactide (including L-lactide, D-lactide, blends thereof, and lactic acid polymers and copolymers) where the mole ratio of trimethylene carbonate to lactide is from about 30:70 to about 70:30; and blends thereof. Examples of suitable biocompatible elastomers are described in U.S. Pat. No. 5,468,253.

In one embodiment, the elastomer is a copolymer of 35:65 ϵ-caprolactone and glycolide, formed in a dioxane solvent and including a polydioxanone mesh. In another embodiment, the elastomer is a copolymer of 40:60 ϵ-caprolactone and lactide with a polydioxanone mesh. In yet another embodiment, the elastomer is a 50:50 blend of a 35:65. copolymer of ϵ-caprolactone and glycolide and 40:60 copolymer of ϵ-caprolactone and lactide. The polydioxanone mesh may be in the form of a one layer thick two-dimensional mesh or a multi-layer thick three-dimensional mesh.

The scaffold of the present invention can, optionally, be formed from a bioresorbable or bioabsorbable material that has the ability to resorb in a timely fashion in the body environment. The differences in the absorption time under in vivo conditions can also be the basis for combining two different copolymers when forming the scaffolds of the present invention. For example, a copolymer of 35:65 ϵ-caprolactone and glycolide (a relatively fast absorbing polymer) can be blended with 40:60 ϵ-caprolactone and L-lactide copolymer (a relatively slow absorbing polymer) to form a biocompatible scaffold. Depending upon the processing technique used the two constituents can be either randomly inter-connected bicontinuous phases, or the constituents could have a gradient-like architecture in the form of a laminate type composite with a well integrated interface between the two constituent layers. The microstructure of these scaffolds can be optimized to regenerate or repair the desired anatomical features of the tissue that is being regrown.

In one embodiment, it is desirable to use polymer blends to form scaffolds which transition from one composition to another composition in a gradient-like architecture. Scaffolds having this gradient-like architecture are particularly advantageous in tissue engineering applications to repair or regenerate the structure of naturally occurring tissue such as cartilage (articular, meniscal, septal, tracheal, auricular, costal, etc.), tendon, ligament, nerve, esophagus, skin, bone, and vascular tissue. For example, by blending an elastomer of ε-caprolactone-co-glycolide with ε-caprolactone-co-lactide (e.g., with a mole ratio of about 5:95) a scaffold may be formed that transitions from a softer spongy material to a stiffer more rigid material, for example, in a manner similar to the transition from cartilage to bone. Clearly, one skilled in the art will appreciate that other polymer blends may be used for similar gradient effects, or to provide different gradients (e.g., different absorption profiles, stress response profiles, or different degrees of elasticity).

The biocompatible scaffold 52 of the tissue repair implant 50 of the present invention can also include a reinforcing material comprised of any absorbable or non-absorbable textile having, for example, woven, knitted, warped knitted (i.e., lace-like), non-woven, and braided structures. In one embodiment, the reinforcing material has a mesh-like structure. In any of the above structures, mechanical properties of the material can be altered by changing the density or texture of the material, the type of knit or weave of the material, the thickness of the material, or by embedding particles in the material. The mechanical properties of the material may also be altered by creating sites within the mesh where the fibers are physically bonded with each other or physically bonded with another agent, such as, for example, an adhesive or a polymer. The fibers used to make the reinforcing component can be monofilaments, yarns, threads, braids, or bundles of fibers. These fibers can be made of any biocompatible material including bioabsorbable materials such as polylactic acid (PLA), polyglycolic acid (PGA), polycaprolactone (PCL), polydioxanone (PDO), trimethylene carbonate (TMC), copolymers or blends thereof. These fibers can also be made from any biocompatible materials based on natural polymers including silk and collagen-based materials. These fibers can also be made of any biocompatible fiber that is nonresorbable, such as, for example, polyethylene, polyethylene terephthalate, poly(tetrafluoroethylene), polycarbonate, polypropylene and poly(vinyl alcohol). In one embodiment, the fibers are formed from 95:5 copolymer of lactide and glycolide.

In another embodiment, the fibers that form the reinforcing material can be made of a bioabsorbable glass. Bioglass, a silicate containing calcium phosphate glass, or calcium phosphate glass with varying amounts of solid particles added to control resorption time are examples of materials that could be spun into glass fibers and used for the reinforcing material. Suitable solid particles that may be added include iron, magnesium, sodium, potassium, and combinations thereof.

The biocompatible scaffolds as well as the reinforcing material may also be formed from a thin, perforation-containing elastomeric sheet with pores or perforations to allow tissue ingrowth. Such a sheet could be made of blends or copolymers of polylactic acid (PLA), polyglycolic acid (PGA), polycaprolactone (PCL), and polydioxanone (PDO).

In one embodiment, filaments that form the biocompatible scaffolds 52 or the reinforcing material may be co-extruded to produce a filament with a sheath/core construction. Such filaments are comprised of a sheath of biodegradable polymer that surrounds one or more cores comprised of another biodegradable polymer. Filaments with a fast-absorbing sheath surrounding a slower-absorbing core may be desirable in instances where extended support is necessary for tissue ingrowth.

One skilled in the art will appreciate that one or more layers of the reinforcing material may be used to reinforce the tissue implant of the invention. In addition, biodegradable textile scaffolds, such as, for example, meshes, of the same structure and chemistry or different structures and chemistries can be overlaid on top of one another to fabricate biocompatible tissue implants with superior mechanical strength.

In embodiments where the scaffold includes at least one natural polymer, suitable examples of natural polymers include, but are not limited to, fibrin-based materials, collagen-based materials, hyaluronic acid-based materials, glycoprotein-based materials, cellulose-based materials, silks and combinations thereof. By way of nonlimiting example, the biocompatible scaffold can be constructed from a collagen-based small intestine submucosa.

By way of non-limiting example, the scaffolds 52 of the present invention can be highly porous to allow cell growth therein. Preferably, the median pore size is in the range of about 100 to 500 microns. In these embodiments, the scaffold should be sufficiently pliable to accommodate tissue growth within the interior region of the scaffold, so that the geometry of the scaffold can be remodeled as tissue ingrowth increases. Accordingly, in the present invention, tissue can be grown on the surface of the biocompatible scaffold, or alternatively, tissue can be grown into and on the surface of the biocompatible scaffold, such that the tissue becomes embedded in and integrated with the scaffold.

In another embodiment of the present invention, the biocompatible scaffold 52 can be formed from a biocompatible ceramic material. Suitable biocompatible ceramic materials include, for example, hydroxyapatite, α-tricalcium phosphate, β-tricalcium phosphate, bioactive glass, calcium phosphate, calcium sulfate, calcium carbonate, xenogeneic and allogeneic bone material and combinations thereof. Suitable bioactive glass materials for use in the present invention include silicates containing calcium phosphate glass, or calcium phosphate glass with varying amounts of solid particles added to control resorption time. Suitable compounds that may be incorporated into the calcium phosphate bioactive glass include, but are not limited to, magnesium oxide, sodium oxide, potassium oxide, and combinations thereof.

In yet another embodiment of the tissue implants of the present invention, the scaffold 52 can be formed using tissue grafts, such as may be obtained from autogeneic tissue, allogeneic tissue and xenogeneic tissue. By way of non-limiting example, tissues such as skin, cartilage, ligament, tendon, periosteum, perichondrium, synovium, fascia, mesenter and sinew can be used as tissue grafts to form the biocompatible scaffold 52. In some embodiments where an allogeneic tissue is used, tissue from a fetus or newborns can be used to avoid the immunogenicity associated with some adult tissues.

In still yet another embodiment of the tissue implants, the scaffold can be formed from a polymeric foam component having pores with an open cell pore structure. The pore size can vary, but preferably, the pores are sized to allow tissue ingrowth. More preferably, the pore size is in the range of about 50 to 1000 microns, and even more preferably, in the range of about 50 to 500 microns. The polymeric foam component can, optionally, contain a reinforcing component, such as for example, the textiles disclosed above. In some embodiments where the polymeric foam component contains a reinforcing component, the foam component can be integrated with the reinforcing component such that the pores of the foam component penetrate the mesh of the reinforcing component and interlock with the reinforcing component.

The foam component of the tissue implant may be formed as a foam by a variety of techniques well known to those having ordinary skill in the art. For example, the polymeric starting materials may be foamed by lyophilization, supercritical solvent foaming (i.e., as described in EP 464,163), gas injection extrusion, gas injection molding or casting with an extractable material (e.g., salts, sugar or similar suitable materials).

In one embodiment, the foam component of the tissue repair implants of the present invention may be made by a polymer-solvent phase separation technique, such as lyophilization. Generally, however, a polymer solution can be separated into two phases by any one of the four techniques: (a) thermally induced gelation/crystallization; (b) non-solvent induced separation of solvent and polymer phases; (c) chemically induced phase separation, and (d) thermally induced spinodal decomposition. The polymer solution is separated in a controlled manner into either two distinct phases or two bicontinuous phases. Subsequent removal of the solvent phase usually leaves a porous structure with a density less than the bulk polymer and pores in the micrometer ranges resulting in a porous polymer structure or an interconnected open cell porous foam. See Microcellular Foams Via Phase Separation, J. Vac. Sci. Technol., A. T. Young, Vol. 4(3), May/June 1986.

The applicable polymer concentration or amount of solvent that may be utilized will vary with each system. Generally, the amount of polymer in the solution can vary from about 0.5% to about 90% and, preferably, will vary from about 0.5% to about 30% by weight, depending on factors such as the solubility of the polymer in a given solvent and the final properties desired in the foam.

In one embodiment, solids may be added to the polymer-solvent system to modify the composition of the resulting foam surfaces. As the added particles settle out of solution to the bottom surface, regions will be created that will have the composition of the added solids, not the foamed polymeric material. Alternatively, the added solids may be more concentrated in desired regions (i.e., near the top, sides, or bottom) of the resulting tissue implant, thus causing compositional changes in all such regions. For example, concentration of solids in selected locations can be accomplished by adding metallic solids to a solution placed in a mold made of a magnetic material (or vice versa).

A variety of types of solids can be added to the polymer-solvent system. Preferably, the solids are of a type that will not react with the polymer or the solvent. Generally, the added solids have an average diameter of less than about 1.0 mm and preferably will have an average diameter of about 50 to about 500 microns. Preferably, the solids are present in an amount such that they will constitute from about 1 to about 50 volume percent of the total volume of the particle and polymer-solvent mixture (wherein the total volume percent equals 100 volume percent).

Exemplary solids include, but are not limited to, particles of demineralized bone, calcium phosphate particles, bioglass particles, calcium sulfate, or calcium carbonate particles for bone repair, leachable solids for pore creation and particles of bioabsorbable polymers not soluble in the solvent system that are effective as reinforcing materials or to create pores as they are absorbed, and non-bioabsorbable materials.

Suitable leachable solids include nontoxic leachable materials such as salts (e.g., sodium chloride, potassium chloride, calcium chloride, sodium tartrate, sodium citrate, and the like), biocompatible mono and disaccharides (e.g., glucose, fructose, dextrose, maltose, lactose and sucrose), polysaccharides (e.g., starch, alginate, chitosan), water soluble proteins (e.g., gelatin and agarose). The leachable materials can be removed by immersing the foam with the leachable material in a solvent in which the particle is soluble for a sufficient amount of time to allow leaching of substantially all of the particles, but which does not dissolve or detrimentally alter the foam. The preferred extraction solvent is water, most preferably distilled-deionized water. Such a process is described in U.S. Pat. No. 5,514,378. Preferably the foam will be dried after the leaching process is complete at low temperature and/or vacuum to minimize hydrolysis of the foam unless accelerated absorption of the foam is desired.

Suitable non-bioabsorbable materials include biocompatible metals such as stainless steel, cobalt chrome, titanium and titanium alloys, and bioinert ceramic particles (e.g., alumina, zirconia, and calcium sulfate particles). Further, the non-bioabsorbable materials may include polymers such as polyethylene, polyvinylacetate, polymethylmethacrylate, polypropylene, polyethylene terephthalate), silicone, polyethylene oxide, polyethylene glycol, polyurethanes, polyvinyl alcohol, natural polymers (e.g., cellulose particles, chitin, and keratin), and fluorinated polymers and copolymers (e.g., polyvinylidene fluoride, polytetrafluoroethylene, and hexafluoropropylene).

It is also possible to add solids (e.g., barium sulfate) that will render the tissue implants radio opaque. The solids that may be added also include those that will promote tissue regeneration or regrowth, as well as those that act as buffers, reinforcing materials or porosity modifiers.

As noted above, porous, reinforced tissue repair implant devices of the present invention are made by injecting, pouring, or otherwise placing, the appropriate polymer solution into a mold set-up comprised of a mold and the reinforcing elements of the present invention. The mold set-up is cooled in an appropriate bath or on a refrigerated shelf and then lyophilized, thereby providing a reinforced scaffold. A bioactive agent can be added either before or after the lyophilization step. In the course of forming the foam component, it is believed to be important to control the rate of freezing of the polymer-solvent system. The type of pore morphology that is developed during the freezing step is a function of factors such as the solution thermodynamics, freezing rate, temperature to which it is cooled, concentration of the solution, and whether homogeneous or heterogenous nucleation occurs. One of ordinary skill in the art can readily optimize the parameters without undue experimentation.

The required general processing steps include the selection of the appropriate materials from which the polymeric foam and the reinforcing components are made. If a mesh reinforcing material is used, the proper mesh density must be selected. Further, the reinforcing material must be properly aligned in the mold, the polymer solution must be added at an appropriate rate and, preferably, into a mold that is tilted at an appropriate angle to avoid the formation of air bubbles, and the polymer solution must be lyophilized.

In embodiments that utilize a mesh reinforcing material, the reinforcing mesh has to be of a certain density. That is, the openings in the mesh material must be sufficiently small to render the construct suturable or otherwise fastenable, but not so small as to impede proper bonding between the foam and the reinforcing mesh as the foam material and the open cells and cell walls thereof penetrate the mesh openings. Without proper bonding the integrity of the layered structure is compromised leaving the construct fragile and difficult to handle. Because the density of the mesh determines the mechanical strength of the construct, the density of the mesh can vary according to the desired use for tissue repair. In addition, the type of weave used in the mesh can determine the directionality of the mechanical strength of the construct, as well as the mechanical properties of the reinforcing material, such as for example, the elasticity, stiffness, burst strength, suture retention strength and ultimate tensile strength of the construct. By way of non-limiting example, the mesh reinforcing material in a foam-based biocompatible scaffold of the present invention can be designed to be stiff in one direction, yet elastic in another, or alternatively, the mesh reinforcing material can be made isotropic.

During the lyophilization of the reinforced foam, several parameters and procedures are important to produce implants with the desired integrity and mechanical properties. Preferably, the reinforcement material is substantially flat when placed in the mold. To ensure the proper degree of flatness, the reinforcement (e.g., mesh) is pressed flat using a heated press prior to its placement within the mold. Further, in the event that reinforcing structures are not isotropic it is desirable to indicate this anisotropy by marking the construct to indicate directionality. This can be accomplished by embedding one or more indicators, such as dyed markings or dyed threads, within the woven reinforcements. The direction or orientation of the indicator will indicate to a surgeon the dimension of the implant in which physical properties are superior.

As noted above, the manner in which the polymer solution is added to the mold prior to lyophilization helps contribute to the creation of a tissue implant with adequate mechanical integrity. Assuming that a mesh reinforcing material will be used, and that it will be positioned between two thin (e.g., 0.75 mm) shims it should be positioned in a substantially flat orientation at a desired depth in the mold. The polymer solution is poured in a way that allows air bubbles to escape from between the layers of the foam component. Preferably, the mold is tilted at a desired angle and pouring is effected at a controlled rate to best prevent bubble formation. One of ordinary skill in the art will appreciate that a number of variables will control the tilt angle and pour rate. Generally, the mold should be tilted at an angle of greater than about 1 degree to avoid bubble formation. In addition, the rate of pouring should be slow enough to enable any air bubbles to escape from the mold, rather than to be trapped in the mold.

If a mesh material is used as the reinforcing component, the density of the mesh openings is an important factor in the formation of a resulting tissue implant with the desired mechanical properties. A low density, or open knitted mesh material, is preferred. One preferred material is a 90:10 copolymer of glycolide and lactide, sold under the tradename VICRYL (Ethicon, Inc., Somerville, N.J.). One exemplary low density, open knitted mesh is Knitted VICRYL VKM-M, available from Ethicon, Inc., Somerville, N.J. Other preferred materials are polydioxanone or 95:5 copolymer of lactide and glycolide.

The density or "openness" of a mesh material can be evaluated using a digital photocamera interfaced with a computer. In one evaluation, the density of the mesh was determined using a Nikon SMZ-U Zoom with a Sony digital photocamera DKC-5000 interfaced with an IBM 300PL computer. Digital images of sections of each mesh magnified to 20× were manipulated using Image-Pro Plus 4.0 software in order to determine the mesh density. Once a digital image was captured by the software, the image was thresholded such that the area accounting for the empty spaces in the mesh could be subtracted from the total area of the image. The mesh density was taken to be the percentage of the remaining digital image. Implants with the most desirable mechanical properties were found to be those with a mesh density in the range of about 12 to 80% and more preferably about 45 to 80%.

In one embodiment, the preferred scaffold for cartilage repair is a mesh reinforced foam. More preferably, the foam is reinforced with a mesh that includes polydioxanone (PDO) and the foam composition is a copolymer of 35:65 ε-caprolactone and glycolide. For articular cartilage, the preferred structure to allow cell and tissue ingrowth is one that has an open pore structure and is sized to sufficiently allow cell migration. A suitable pore size is one in which an average diameter is in the range of about 50 to 1000 microns, and more preferably, between about 50 to 500 microns. The mesh layer has a thickness in the range of about 1 micron to 1000 microns. Preferably, the foam has a thickness in the range of about 300 microns to 2 mm, and more preferably, between about 500 microns and 1.5 mm. Preferably, the mesh layer has a mesh density in the range of about 12 to 80% and more preferably about 45 to 80%.

In another embodiment, the preferred scaffold for cartilage repair is a nonwoven structure. More preferably, the composition of the nonwoven structure are PANACRYL, a 95:5 copolymer of lactide and glycolide, VICRYL, a 90:10 copolymer of glycolide and lactide, or a blend of polydioxanone and VICRYL. For articular cartilage, the preferred structure to allow cell and tissue ingrowth is one that has an open pore structure and is sized to sufficiently allow cell migration. A suitable pore size for the nonwoven scaffold is one in which an average diameter is in the range of about 50 to 1000 microns and more preferably between about 100 to 500 microns. The nonwoven scaffold has a thickness between about 300 microns and 2 mm, and more preferably, between about 500 microns and 1.5 mm.

In yet another embodiment, the preferred scaffold for meniscus repair is a mesh reinforced foam. More preferably, the foam is reinforced foam with a mesh that includes polydioxanone (PDO) and the foam composition is a copolymer of 35:65 ε-caprolactone and glycolide. The preferred structure to allow cell and tissue ingrowth is one that has an open pore structure and is sized to sufficiently allow cell migration. A suitable pore size is one in which an average diameter is in the range of about 50 to 1000 microns, and more preferably, between about 50 to 500 microns. The mesh layer has a thickness in the range of about 1 micron to 1000 microns. Preferably, the foam has a thickness in the range of about 300 microns to 2 mm, and more preferably, between about 500 microns and 1.5 mm. In this embodiment, the preferred method of use is to surround the minced cartilage tissue with this scaffold material. Preferably, the mesh layer has a mesh density in the range of about 12 to 80% and more preferably about 45 to 80%.

In still yet another embodiment, the preferred scaffold for tissue repair, including cartilage, meniscus, tendon, ligament, and skin repair, is constructed from a naturally occurring extracellular matrix material ("ECM"), such as that found in the stomach, bladder, alimentary, respiratory, urinary, integumentary, genital tracts, or liver basement membrane of animals. Preferably, the ECM is derived from the alimentary tract of mammals, such as cows, sheeps, dogs, cats, and most preferably from the intestinal tract of pigs. The ECM is preferably small intestine submucosa ("SIS"), which can include the tunica submucosa, along with basilar portions of the tunica mucosa, particularly the lamina muscularis mucosa and the stratum compactum.

For the purposes of this invention, it is within the definition of a naturally occurring ECM to clean and/or comminute the ECM, or even to cross-link the collagen fibers within the ECM. However, it is not within the definition of a naturally occurring ECM to extract and purify the natural fibers and reform a matrix material from purified natural fibers. Also, while reference is made to SIS, it is understood that other naturally occurring ECMs are within the scope of this invention. Thus, as used herein, the terms "naturally occurring extracellular matrix" or "naturally occurring ECM" are intended to refer to extracellular matrix material that has been cleaned, disinfected, sterilized, and optionally cross-linked.

Where SIS is used, a SIS graft can be harvested in a variety of ways, as will be understood by one skilled in the art. The resulting graft material can have a variety of geometries and consistencies including for example, coiled, helical, spring-like, randomized, branched, sheet-like, tubular, spherical, fragmented, fluidized, comminuted, liquefied, flamed, suspended, gel-like, injectable, powdered, ground, and sheared.

One of ordinary skill in the art will appreciate that the selection of a suitable material for forming the biocompatible scaffold of the present invention depends on several factors. These factors include in viva mechanical performance; cell response to the material in terms of cell attachment, proliferation, migration and differentiation; biocompatibility; and optionally, bioabsorption (or bio-degradation) kinetics. Other relevant factors include the chemical composition, spatial distribution of the constituents, the molecular weight of the polymer, and the degree of crystallinity.

A bioactive agent may, optionally, be incorporated within the tissue scaffolds 52 of the present invention. Preferably, the bioactive agent is incorporated within, or coated on, the scaffolds 52 disclosed above. In embodiments where the bioactive agent is coated onto the scaffold 52, the bioactive agent is preferably associated with at least a portion of the scaffold 52. The bioactive agents used in the present invention can also be selected from among a variety of effectors that, when present at the site of injury, promote healing and/or regeneration of the affected tissue. In addition to being compounds or agents that actually promote or expedite healing, the effectors may also include compounds or agents that prevent infection (e.g., antimicrobial agents and antibiotics), compounds or agents that reduce inflammation (e.g., anti-inflammatory agents), compounds that prevent or minimize adhesion formation, such as oxidized regenerated cellulose (e.g., INTERCEED and Surgicel®, available from Ethicon, Inc.), hyaluronic acid, and compounds or agents that suppress the immune system (e.g., immunosuppressants).

By way of example, other types of effectors present within the implant of the present invention can include heterologous or autologous growth factors, proteins (including matrix proteins), peptides, antibodies, enzymes, platelets, platelet rich plasma, glycoproteins, hormones, cytokines, glycosaminoglycans, nucleic acids, analgesics, viruses, virus particles, and cell types. It is understood that one or more effectors of the same or different functionality may be incorporated within the implant.

Examples of suitable effectors include the multitude of heterologous or autologous growth factors known to promote healing and/or regeneration of injured or damaged tissue. These growth factors can be incorporated directly into the scaffold, or alternatively, the scaffold can include a source of growth factors, such as for example, platelets. "Bioactive agents," as used herein, include one or more of the following: chemotactic agents; therapeutic agents (e.g., antibiotics, steroidal and non-steroidal analgesics and anti-inflammatories, anti-rejection agents such as immunosuppressants and anti-cancer drugs); various proteins (e.g., short term peptides, bone morphogenic proteins, glycoprotein and lipoprotein); cell attachment mediators; biologically active ligands; integrin binding sequence; ligands; various growth and/or differentiation agents and fragments thereof (e.g., epidermal growth factor (EGF), hepatocyte growth factor (HGF), vascular endothelial growth factors (VEGF), fibroblast growth factors (e.g., bFGF), platelet derived growth factors (PDGF), insulin derived growth factor (e.g., IGF-I, IGF-II) and transforming growth factors (e.g., TGF-β I-III), parathyroid hormone, parathyroid hormone related peptide, bone morphogenetic proteins (e.g., BMP-2, BMP-4; BMP-6; BMP-12), sonic hedgehog, growth differentiation factors (e.g., GDF5, GDF6, GDF8), recombinant human growth factors (e.g., MP52), cartilage-derived morphogenetic proteins, (CDMP1)); small molecules that affect the upregulation of specific growth factors; tenascin-C; hyaluronic acid; chondroitin sulfate; fibronectin; decorin; thromboelastin; thrombin-derived peptides; heparin-binding domains; heparin; heparan sulfate; DNA fragments and DNA plasmids. Suitable effectors likewise include the agonists and antagonists of the agents described above. The growth factor can also include combinations of the growth factors described above. In addition, the growth factor can be autologous growth factor that is supplied by platelets in the blood. In this case, the growth factor from platelets will be an undefined cocktail of various growth factors. If other such substances have therapeutic value in the orthopaedic field, it is anticipated that at least some of these substances will have use in the present invention, and such substances should be included in the meaning of "bioactive agent" and "bioactive agents" unless expressly limited otherwise.

Biologically derived agents, suitable for use as effectors, include one or more of the following: bone (autograft, allograft, and xenograft) and derivates of bone; cartilage (autograft, allograft and xenograft), including, for example, meniscal tissue, and derivatives; ligament (autograft, allograft and xenograft) and derivatives; derivatives of intestinal tissue (autograft, allograft and xenograft), including for example submucosa; derivatives of stomach tissue (autograft, allograft and xenograft), including for example submucosa; derivatives of bladder tissue (autograft, allograft and xenograft), including for example submucosa; derivatives of alimentary tissue (autograft, allograft and xenograft), including for example submucosa; derivatives of respiratory tissue (autograft, allograft and xenograft), including for example submucosa; derivatives of genital tissue (autograft, allograft and xenograft), including for example submucosa; derivatives of liver tissue (autograft, allograft and xenograft), including for example liver basement membrane; derivatives of skin tissue; platelet rich plasma (PRP), platelet poor plasma, bone marrow aspirate, demineralized bone matrix, insulin derived growth factor, whole blood, fibrin and blood clot. Purified ECM and other collagen sources are also appropriate biologically derived agents. If other such substances have therapeutic value in the orthopaedic field, it is anticipated that at least some of these substances will have use in the present invention, and such substances should be included in the meaning of "biologicallyderived agent" and "biologicallyderived agents" unless expressly limited otherwise.

Biologically derived agents also include bioremodelable collageneous tissue matrices. The terms "bioremodelable collagenous tissue matrix" and "naturally occurring bioremodelable collageneous tissue matrix" include matrices derived from native tissue selected from the group consisting of skin, artery, vein, pericardium, heart valve, dura mater, ligament, bone, cartilage, bladder, liver, stomach, fascia and intestine, whatever the source. Although the term "naturally occurring bioremodelable collageneous tissue matrix" is intended to refer to matrix material that has been cleaned, processed, sterilized, and optionally crosslinked, it is not within the definition of a naturally occurring bioremodelable collageneous tissue matrix to purify the natural fibers and reform a matrix material from purified natural fibers.

The proteins that may be present within the implant include proteins that are secreted from a cell or other biological source, such as for example, a platelet, which is housed within the implant, as well as those that are present within the implant in an isolated form. The isolated form of a protein typically is one that is about 55% or greater in purity, i.e., isolated from other cellular proteins, molecules, debris, etc. More preferably, the isolated protein is one that is at least 65% pure, and most preferably one that is at least about 75 to 95% pure. Notwithstanding the above, one of ordinary skill in the art will appreciate that proteins having a purity below about 55% are still considered to be within the scope of this invention. As used herein, the term "protein" embraces glycoproteins, lipoproteins, proteoglycans, peptides, and fragments thereof. Examples of proteins useful as effectors include, but are not limited to, pleiotrophin, endothelin, tenascin, fibronectin, fibrinogen, vitronectin, V-CAM, I-CAM, N-CAM, selectin, cadherin, integrin, laminin, actin, myosin, collagen, microfilament, intermediate filament, antibody, elastin, fibrillin, and fragments thereof.

Glycosaminoglycans, highly charged polysaccharides which play a role in cellular adhesion, may also serve as effectors according to the present invention. Exemplary glycosaminoglycans useful as effectors include, but are not limited to, heparan sulfate, heparin, chondroitin sulfate, dermatan sulfate, keratan sulfate, hyaluronan (also known as hyaluronic acid), and combinations thereof.

The tissue scaffolds 52 of the present invention can also have cells incorporated therein. Suitable cell types that can serve as effectors according to this invention include, but are not limited to, osteocytes, osteoblasts, osteoclasts, fibroblasts, stem cells, pluripotent cells, chondrocyte progenitors, chondrocytes, endothelial cells, macrophages, leukocytes, adipocytes, monocytes, plasma cells, mast cells, umbilical cord cells, stromal cells, mesenchymal stem cells, epithelial cells, myoblasts, tenocytes, ligament fibroblasts, neurons, bone marrow cells, synoviocytes, embryonic stem cells; precursor cells derived from adipose tissue; peripheral blood progenitor cells; stem cells isolated from adult tissue; genetically transformed cells; a combination of chondrocytes and other cells; a combination of osteocytes and other cells; a combination of synoviocytes and other cells; a combination of bone marrow cells and other cells; a combination of mesenchymal cells and other cells; a combination of stromal cells and other cells; a combination of stem cells and other cells; a combination of embryonic stem cells and other cells; a combination of precursor cells isolated from adult tissue and other cells; a combination of peripheral blood progenitor cells and other cells; a combination of stem cells isolated from adult tissue and other cells; and a combination of genetically transformed cells and other cells. If other cells are found to have therapeutic value in the orthopaedic field, it is anticipated that at least some of these cells will have use in the present invention, and such cells should be included within the meaning of "cell" and "cells" unless expressly limited.

Cells typically have at their surface receptor molecules which are responsive to a cognate ligand (e.g., a stimulator). A stimulator is a ligand which when in contact with its cognate receptor induce the cell possessing the receptor to produce a specific biological action. For example, in response to a stimulator (or ligand) a cell may produce significant levels of secondary messengers, like $Ca^{+2}$, which then will have subsequent effects upon cellular processes such as the phosphorylation of proteins, such as (keeping with our example) protein kinase C. In some instances, once a cell is stimulated with the proper stimulator, the cell secretes a cellular messenger usually in the form of a protein (including glycoproteins, proteoglycans, and lipoproteins). This cellular messenger can be an antibody (e.g., secreted from plasma cells), a hormone, (e.g., a paracrine, autocrine, or exocrine hormone), a cytokine, or natural or synthetic fragments thereof.

The tissue implants 50 of the invention can also be used in gene therapy techniques in which nucleic acids, viruses, or virus particles deliver a gene of interest, which encodes at least one gene product of interest, to specific cells or cell types. Accordingly, the biological effector can be a nucleic acid (e.g., DNA, RNA, or an oligonucleotide), a virus, a virus particle, or a non-viral vector. The viruses and virus particles may be, or may be derived from, DNA or RNA viruses. The gene product of interest is preferably selected from the group consisting of proteins, polypeptides, interference ribonucleic acids (iRNA) and combinations thereof.

Once the applicable nucleic acids and/or viral agents (i.e., viruses or viral particles) are incorporated into the biocompatible scaffold of the tissue repair implant, the implant can then be implanted into a particular site to elicit a type of biological response. The nucleic acid or viral agent can then be taken up by the cells and any proteins that they encode can be produced locally by the cells. In one embodiment, the nucleic acid or viral agent can be taken up by the cells within the tissue fragment of the minced tissue suspension, or, in an alternative embodiment, the nucleic acid or viral agent can be taken up by the cells in the tissue surrounding the site of the injured tissue. One skilled in the art will recognize that the protein produced can be a protein of the type noted above, or a similar protein that facilitates an enhanced capacity of the tissue to heal an injury or a disease, combat an infection, or reduce an inflammatory response. Nucleic acids can also be used to block the expression of unwanted gene product that may impact negatively on a tissue repair process or other normal biological processes. DNA, RNA and viral agents are often used to accomplish such an expression blocking function, which is also known as gene expression knock out.

One of ordinary skill in the art will appreciate that the identity of the bioactive agent may be determined by a surgeon, based on principles of medical science and the applicable treatment objectives. It is understood that the bioactive agent or effector of the issue repair implant can be incorporated within the tissue scaffold 52 before or after manufacture of the tissue scaffold 52, or before or after the surgical placement of the implant 50.

Prior to surgical placement, the tissue scaffold 52 can be placed in a suitable container comprising the bioactive agent. After an appropriate time and under suitable conditions, the scaffold 52 will become impregnated with the bioactive agent. Alternatively, the bioactive agent can be incorporated within the scaffold 52 by, for example, using an appropriately gauged syringe to inject the biological agent(s) into the scaffold. Other methods well known to those of skilled in the art can be applied in order to load a scaffold 52 with an appropriate bioactive agent, such as mixing, pressing, spreading, centrifuging and placing the bioactive agent into the scaffold 52. Alternatively, the bioactive agent can be mixed with a gel-like carrier prior to injection into the scaffold 52.

Following surgical placement, an implant wherein the biocompatible scaffold 52 is devoid of any bioactive agent can be infused with biological agent(s), or an implant wherein the scaffold includes at least one bioactive agent can be augmented with a supplemental quantity of the bioactive agent.

One method of incorporating a bioactive agent within a surgically installed implant is by injection using an appropriately gauged syringe.

The amount of the bioactive agent included with a biocompatible scaffold 52 will vary depending on a variety of factors, including the size of the scaffold, the material from which the scaffold is made, the porosity of the scaffold, the identity of the biologically component, and the intended purpose of the tissue repair implant. One skilled in the art can readily determine the appropriate quantity of bioactive agent to include within a biocompatible scaffold for a given application in order to facilitate and/or expedite the healing of tissue. The amount of bioactive agent will, of course, vary depending upon the identity of the bioactive agent and the given application.

The tissue repair implants of the present invention can be used in a variety of surgical and non-surgical applications. In some surgical applications, such as for use in the repair of a variety of tissues including a torn ligament, tendon, rotator cuff; nerve, skin, cartilage, or meniscus, the tissue implants of the invention must be able to be handled in the operating room, and they must be able to be sutured or otherwise fastened without tearing. Additionally, the implants should have a structure suitable to encourage tissue ingrowth.

In one embodiment of the present invention, the tissue repair implant is used in the treatment of a tissue injury, such as injury to a ligament, tendon, nerve, skin, cartilage or meniscus. Repairing tissue injuries involves the steps of obtaining a slice of living tissue 22 by any of the variety of techniques known to those skilled in the art, and placing the tissue slice 22 in a desired position relative to the tissue injury. While a single tissue slice 22 can be used, more than one tissue slice 22 can be joined together to form a layered implant 40 for implantation. Repairing tissue injuries may also involve depositing the tissue slice 22 onto a biocompatible, bioabsorbable tissue scaffold 52 such that the tissue slice 22 becomes associated with the scaffold 52 to form a tissue repair implant 50. A retaining element 30 can optionally be applied to secure the implant to the injury or defect 10. In an additional step, finely minced tissue fragments can be applied to the implant to enhance the effectiveness of the regrowth and healing process. The cells in both the tissue slices and minced tissue fragments can migrate out and begin proliferating and integrating with surrounding tissue at the site of implantation, thereby repairing the tissue injury. This method for repairing tissue injuries can include an additional, optional step. Prior to the step of placing the tissue repair implant in a desired position relative to the tissue injury, the scaffold and associated tissue particles can be incubated for a duration and under conditions effective to allow cells within the tissue particles to migrate from the tissue and begin populating the scaffold.

The implants used to repair injured tissue can be of a size and shape such that they match the geometry and dimensions of a desired portion or lesion of the tissue to be treated. The implant can be sized and shaped to produce the necessary geometry by numerous techniques including cutting, folding, rolling, or otherwise manipulating the implant. As noted above, the bioactive agent may be added to the scaffold during or after manufacture of the scaffold or before or after the implant is installed in a patient. An additional quantity of the bioactive agent may be added after the implant is installed. Once access is made into the affected anatomical site (whether by minimally invasive, open or mini-open surgical technique), the implant can be affixed to a desired position relative to the tissue injury, such as within a tear or lesion. Once the implant is placed in the desired position or lesion, it can be affixed by using an appropriate retaining element 30 or other suitable technique. In one aspect, the implant can be affixed by a chemical and/or mechanical fastening technique. Suitable chemical fasteners include glues and/or adhesive such as fibrin glue, fibrin clot, and other known biologically compatible adhesives. Suitable mechanical fasteners include sutures, staples, tissue tacks, suture anchors, darts, screws, pins and arrows. It is understood that combinations of one or more chemical and/or mechanical fasteners can be used. Alternatively, one need not use any chemical and/or mechanical fasteners. Instead, placement of the implant can be accomplished through an interference fit of the implant with an appropriate site in the tissue to be treated.

In one use, the tissue repair implant can be for repair and to augment tissue loss during tendon or ligament repair surgery or it can be used as a stand alone device. In the case of repair, tendon or ligament ends are approximated through appropriate surgical techniques and the tissue repair implant is used around the joined end to give more mechanical support and to enhance the healing response. As a result of the healing process, the tendon or ligament tissue grows within the implant device, eventually maturing into a tissue with similar mechanical properties to that of native tissue. The implant provides the mechanical support that is initially necessary to ensure proper healing, and it also serves as a guide for tissue regeneration. In another use as a stand alone device, the ruptured tissue is removed, and the tissue repair implant with sliced tissue serves to replace the function of the damaged tissue. In one embodiment, the ruptured tissue can be the tissue source used for healing damaged tissue.

In embodiments where the tissue repair implant is used to repair ligament tissue, the tissue repair implant can be used for tissue augmentation, or alternatively, as a stand-alone device. In embodiments where the tissue repair implant is used for augmentation, the tissue repair implant can be used in conjunction with any of a variety of standard, established repair techniques known to those skilled in the art. In embodiments where the tissue repair implant is used for augmentation during ACL repair, surgeons currently use an autograft consisting of ligament tissue, bone-patellar tendons, tendon-bone tendons, hamstring tendons, or iliotibial band to repair tissue, and the tissue repair implant of the present invention can be placed either around the autograft, surrounded by the autograft, or alongside the autograft. In embodiments where the tissue repair element is used as a stand-alone device, the ruptured ligament can be removed and completely replaced by the tissue repair implant. In this case, the tissue repair implant can be affixed to bone at each end of the implant. In the case of ACL repair, one end of the implant can be stabilized at the original origin site of the femur, while the other end can be placed at the original insertion site on the tibia.

The tissue repair implant can be utilized in a variety of configurations. For example, the implant can be composed of long pieces of tissue, folded or stacked in multiple laminates, or it can be rolled into the shape or a tube-like structure. Tendon or ligament ends can be joined, for example, by suturing, stapling, clipping, adhering, or anchoring, the implant to ends of the implant. In some embodiments where the tissue repair implant is used to repair tendons, such as for example, rotator cuff repair, the surgeon can use the tissue repair implant to assist in the reapproximation of the torn rotator cuff to a bony trough through the cortical surface of the greater tuberosity. Often times, in older patients, the rotator cuff tissue is thin and degenerate and/or the quality of the humerus is osteoporotic. Therefore, in order to increase the strength of the attachment to the bony trough, the tissue repair implant can be placed on top of the tendon, such that the sutures would pass through both the scaffold and tendon, or alternatively, the tissue repair implant can be used on top of the bone bridge to prevent the sutures from pulling out of the bone. In either embodiment, the tissue repair implant provides suture retention strength. In situations where the quality of the rotator cuff is so degenerate that the tissue cannot be reapproximated to the humerus, the tissue repair implant can serve as a bridge, wherein one end of the implant can be joined to the remaining tendon while the other end can be attached to the bone.

In another variation, the implant can be used to repair or replace the sheath of a tendon. To do so, the implant is sutured or otherwise joined to the connective tissue, such as the periosteum, synovium, or muscle, or wrapped around the tendon. This construction allows free gliding of the tendon within the sheath formed by the implant. The implant provides the necessary structural support following surgery. Over time, however, the implant in this embodiment can be resorbed and replaced by new tissue.

The implants of the invention can also be used for organ repair replacement or regeneration strategies that may benefit from these unique tissue implants. For example, these implants can be used for spinal disc, cranial tissue, dura, nerve tissue, liver, pancreas, kidney, bladder, uterus, esophagus, liver spleen, cardiac muscle, skeletal muscle, skin, fascia, pelvic floor, stomach, tendons, cartilage, ligaments, and breast tissues.

The implants of the present invention can also be used as a delivery device for a therapeutic, wherein the therapeutic is the minced tissue, which includes a combination of cells, extracellular matrix and inherent growth factors. The scaffold portion of the implant can allow for hormones and proteins to be released into the surrounding environment.

The methods of repairing tissue injuries using the tissue implants according to the present invention can be conducted during a surgical operation to repair the tissue injury. In an exemplary method, a patient is prepared for tissue repair surgery in a conventional manner using conventional surgical techniques. Tissue repair is performed at the site of the defective or injured tissue 10 using the composite tissue implant 50 of the present invention. The tissue slice 22 used to form the tissue implant 50 is obtained from the patient (or another donor) using appropriate tools and techniques. The tissue slice 22 is either harvested with a specified geometry suitable for the defect or injury 10 or cut into the specified geometry after harvest. The method of harvesting or cutting into the specified geometry can be done with a conventional sterile surgical instruments or a specially designed device. The prepared tissue slice is then applied to a tissue scaffold 52. The scaffold and tissue can then be implanted at the site of tissue injury using a retaining element 30 such as sutures, staples, an adhesive agent, mechanical force or any other fixation device. Final wound closure is performed in a conventional manner using conventional surgical techniques.

The following examples are illustrative of the principles and practice of this invention. Numerous additional embodiments within the scope and spirit of the invention will become apparent to those skilled in the art.

EXAMPLE 1

In this in vitro study, cellular migration and new matrix formation from minced and shredded bovine anterior cruciate ligament (ACL) tissue into non-woven tissue scaffold (PANACRYL) was evaluated and compared. Pre-scored and sterilized PANACRYL non-woven sheets were trimmed to yield two (2) 2.5×2 cm sheets. Next, bovine ACL tissue samples were obtained from two knees from the same animal. To prepare the shredded tissue, an isolated section of the bovine ACL was trimmed under aseptic conditions to measure approximately 2×2×0.5 cm in overall dimensions. Using a sterile scalpel, multiple full thick incisions were made parallel to the fibers of the ACL section, yielding tissue strands measuring approximately 2 cm in length and 0.1 cm in maximum diameter. The tissue strands were placed parallel to the long axis of a PANACRYL sheet to form a composite implant. To prepare the control, minced ACL tissue fragments were also applied to a sheet of PANACRYL. The minced tissue fragments were obtained by mincing the bovine ACL tissue sample using scalpel blades to obtain small tissue fragments. Both the composite implant and the control were placed in Dulbecco's modified eagles medium (DMEM), supplemented with 20% fetal bovine serum (FBS). After 4 days and 21 days, a DNA assay was performed and the histology of the samples were evaluated.

Results

After 4 days and 21 days, the samples were prepared for histological evaluation. Five-micron sections were obtained and adhered to glue coated slides. These sections were then stained with hematoxylin and eosin. In addition, the DNA content of each sample was obtained by assay using a Molecular Probes CyQUANT Cell Proliferation Assay kit (cat. no. C-7026). 5 mm bunch biopsy samples of the composite implant were obtained at day 4 and day 21. The samples were washed once in 1× PBS and frozen at −20° C. for at least one hour. The samples were then thawed at room temperature and incubated in 40 μl of 4M Guanidine-HCL. 10 μl of the guanidine digested sample was added to 190 μl of CyQUANT GR working solution. The mixture was vortexed and incubated for 5 minutes, and then loaded into a 96-well black walled plate and analyzed by spectrophotometry. The results of the DNA assay are shown in Table 1 below.

In the control sample with the minced tissue, the cells within the minced tissue appeared viable after 4 days, while no cells were noted within the tissue scaffold. After 21 days, an evenly distributed sparse cell population was noted within the scaffold. The foci of what appeared to be early new matrix formation was noted along the tissue-scaffold junction.

In the shredded tissue implant, the cells within the shredded tissue appeared viable after 4 days, while no cells were observed within the tissue scaffold. After 21 days, an evenly distributed sparse cell population was noted within the scaffold. The foci of what appeared to be early new matrix formation was noted along the tissue-scaffold junction.

TABLE 1

Comparison of DNA content in minced v. shredded tissue
DNA assay:

| | DNA (ng) | | | |
|---|---|---|---|---|
| sample | day 4 | day 4 avg. | day 21 | day 21 avg. |
| Minced | 4420 | 4284 | 5256 | 4853.66667 |
| | 4198 | | 3862 | |
| | 4234 | | 5443 | |
| Shredded | 1793 | 2033.333 | 2400 | 2680.66667 |
| | 2074 | | 2219 | |
| | 2233 | | 3423 | |

Figure 5:
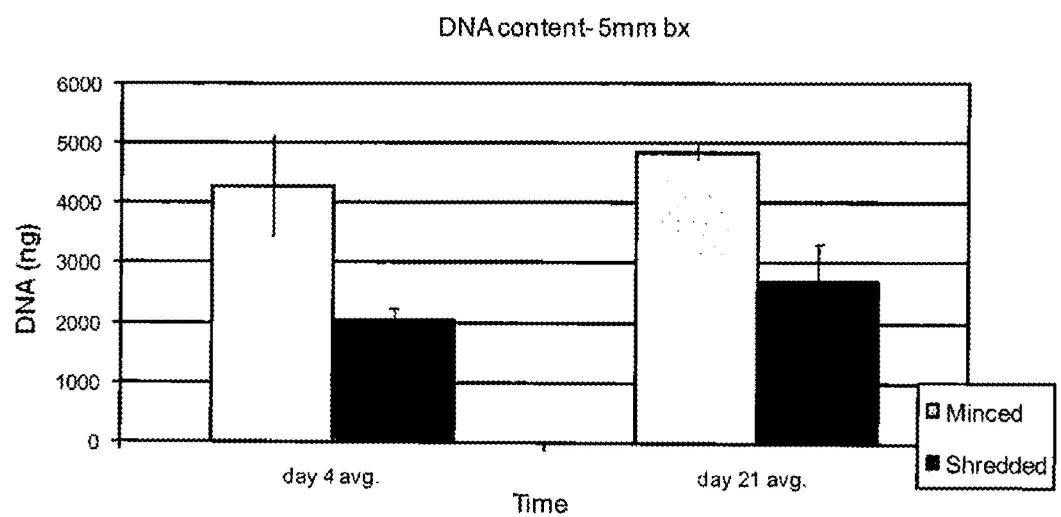
FIG. 5 represents a bar chart comparing DNA content between shredded bovine ACL tissue and minced bovine ACL tissue fragments seeded onto a tissue scaffold in vitro, at 4 days and 21 days.

The data from Table 1 is also graphically presented in FIG. 5 as a bar chart for ease of comparison.

Discussion

As indicated by the histological evaluation of the samples, the cells of the shredded ACL tissue were able to migrate into the tissue scaffold and show early signs of matrix formation at 21 days. Shredded ACL tissue also appeared to function similarly to minced ACL tissue fragments in that both tissue geometries exhibited the same cell population and distribution profile at 21 days.

As indicated by the DNA assays performed, the relative increase in DNA content noted in the shredded ACL tissue appears similar to the increase in DNA content noted in the minced ACL tissue. These results are consistent with the histological data.

It was concluded that sparse and evenly distributed cell migration and focal new matrix formation can be observed in PANACRYL non-woven scaffolds seeded with shredded bovine ACL tissue at 21 days. These results are similar to minced bovine ACL tissue fragments seeded onto the same scaffold at 21 days.

EXAMPLE 2

In this in vitro study, sliced meniscal tissue was tested as a source of viable cells for meniscal regeneration. First, an isolated bovine meniscus was obtained and trimmed to remove the surrounding synovium. Using a sterile dermatome, slices of meniscus were removed. The thickness of the slices were either 200 μm, 300 μm or 500 μm. The slices were approximately 1 to 2 cm in length. The meniscal slices were seeded onto scaffolds comprising sterilized, 65:35 polyglycolic acid/poly caprolactone acide foam reinforced with polydioxone mesh at a density of 20 mg/cm$^2$. The scaffolds measured 4×2.5 cm. Platelet rich plasma (PRP) was added to the scaffolds at a concentration of 20 μl/cm$^2$ and the scaffolds cultured for 3 and 5 weeks in Dulbecco's modified eagles medium (DMEM) supplemented with 0.5% fetal bovine serum (FBS). After 3 and 5 weeks, the samples were prepared for histological evaluation. Sections of the samples were obtained and stained with hematoxylin and eosin.

Results

FIGS. 6A and 6B demonstrate migration of viable fibrochondrocytes from tissue slices of 200 μm (FIG. 6A) and 300 μm thickness (FIG. 6B), at 3 weeks. FIG. 6C shows similar cell migration from 500 μm thick tissue at 3 weeks. At 5 weeks, similar cell migration patterns were observed for each of the varying tissue slices.

Discussion

The study shows that cells in the sliced meniscal tissue were viable and able to migrate into and populate tissue scaffolds associated with the sliced tissue. In addition, the variation in thickness of the slices did not appear to have a qualitative difference in the cell population in the scaffolds.

EXAMPLE 3

In this in vitro study, minced tissue fragments were used in conjunction with mosaicplasty techniques to demonstrate that better integration between cartilage plugs can be achieved and cartilage repair of damaged tissue can be enhanced by the addition of minced cartilage fragments.

Figure 7A:
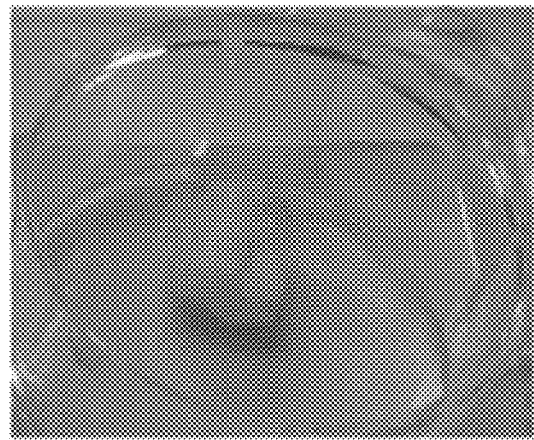
FIG. 7A is a photograph of a cartilage sample obtained following the procedure of EXAMPLE 3, demonstrating that minced cartilage fragments combined with cartilage tissue plugs enhance cell migration in spaces between the fragments and the plugs.
Figure 7B:
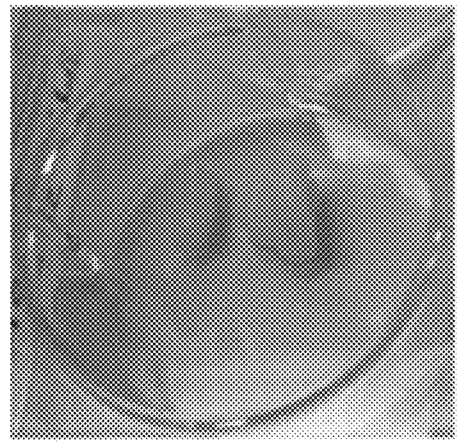
FIG. 7B is a photograph of a cartilage sample obtained following the procedure of EXAMPLE 3, demonstrating that cartilage plugs cultured together as a bundle, without minced cartilage tissue fragments, did not bond together.
Figure 7C:
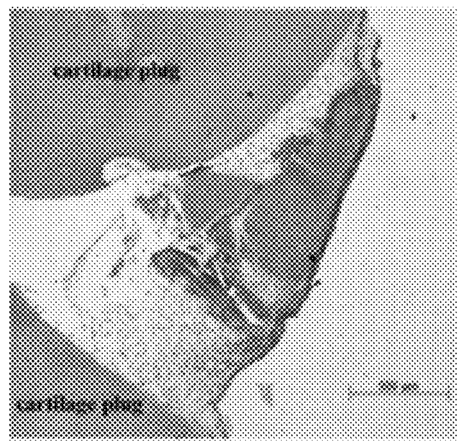
FIG. 7C is a photomicrograph of a histological section of the sample of FIG. 7A, demonstrating cell migration in the space between the minced cartilage fragments and the cartilage plugs.

Healthy articular cartilage was obtained from bovine stifle. A 3 mm biopsy punch was used to punch cylinders or plugs of cartilage tissue. The rest of the cartilage tissue, which was substantially free of bone, was minced using scalpel blades to obtain small tissue fragments. The size of the tissue fragments varied but was less than or equal to 1×1 mm in dimension. Four 3 mm cartilage cylinders were placed together in parallel to each other longitudinally in a glass cylinder with an inner diameter of 8 mm. In one group, a blood clot was then formed inside the glass cylinder to keep the tissues together. In another group, the minced cartilage tissue was placed in the glass cylinder with four 3 mm cartilage cylinders and then a blood clot was formed inside to keep everything together. The glass cylinders were slipped off and the tissue-clot was placed in culture in 6 well plates containing chondrocyte growth medium. The chondrocyte growth medium consisted of Dulbecco's modified eagles medium (DMEM-high glucose) supplemented with 10% fetal calf serum (FCS), 10 mM HEPES, 0.1 mM nonessential amino acids, 20 mg/ml of L-proline, 50 mg/ml ascorbic acid, 100 mg/ml penicillin, 100 mg/ml of streptomycin. The growth medium was changed every other day. The tissues were cultured at 37° C. in a cell culture incubator for six weeks. Samples were removed, macroscopic pictures were taken, and then the samples were placed in formalin for histology. Sections were stained with H&E and Safranin-O. FIG. 7A is a photograph of the group with minced tissue which shows that all the tissues are held together. Histology of this sample confirmed that cells from both the minced tissue and cylinders were migrating into the space between the tissue cylinders, keeping the whole entity together (FIG. 7C). FIG. 7B is a photograph of the group without the minced tissue, showing that after 3 weeks in culture the cartilage cylinders began pulling away from each other because there was nothing that was bonding them together.

Discussion

This study shows that the addition of minced cartilage fragments to closely associated cartilage plugs or cylinders can produce better cellular integration between the plugs. While cartilage cylinders were used in the present example, it is contemplated that the same mosaicplasty principles can be applied to the present invention to provide a tissue repair implant comprising tissue slices and minced tissue fragments for enhanced cellular integration and tissue repair.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A biocompatible tissue implant for repairing a tissue injury or defect, comprising:

(i) a biological tissue slice having a geometry suitable for implantation at the tissue site, the tissue slice being capable of acting as a source of an effective amount of viable cells, and further being dimensioned so that the cells can migrate out of the tissue slice to proliferate and integrate with tissue at the injury or defect, and (ii) at least one minced tissue fragment associated with the tissue slice and containing a plurality of viable cells.

2. The implant of claim 1, wherein the tissue slice comprises autogeneic tissue, allogeneic tissue, xenogeneic tissue, and combinations thereof.

3. The implant of claim 1, wherein the tissue slice is obtained from a tissue type selected from the group consisting of cartilage, meniscus, tendon, ligament, intestinal, stomach, bladder, alimentary, respiratory, genital, liver, dermis, synovium, and combinations thereof.

4. The implant of claim 1, wherein the tissue slice has a thickness less than about 3 mm.

5. The implant of claim 4, wherein the tissue slice has a thickness less than about 1 mm.

6. The implant of claim 5, wherein the tissue slice has a thickness in the range of about 200 μm to about 500 μm.

7. The implant of claim 1, further including a plurality of tissue slices joined together to form a layered implant of a desired size and geometry.

8. The implant of claim 1, further including a retaining element for securing the tissue slice to the tissue site.

9. The implant of claim 1, wherein the at least one minced tissue fragment has a particle size in the range of about 0.1 $mm^3$ to about 2 $mm^3$.

10. The implant of claim 1, further including a biocompatible tissue scaffold.

11. The implant of claim 10, wherein the tissue scaffold is bioresorbable.

12. The implant of claim 10, wherein the tissue scaffold is formed from a material selected from the group consisting of a synthetic polymer, a natural polymer, an injectable gel, a ceramic material, autogeneic tissue, allogeneic tissue, xenogeneic tissue, and combinations thereof.

13. The implant of claim 10, wherein the scaffold further comprises at least one bioactive agent applied thereto.

14. The implant of claim 13, wherein the at least one bioactive agent is selected from the group consisting of growth factors, matrix proteins, peptides, antibodies, enzymes, platelets, platelet rich plasma, glycoproteins, hormones, glycosaminoglycans, nucleic acids, analgesics, viruses, virus particles, cytokines and isolated cells and combinations thereof.

15. The implant of claim 10, further including a plurality of tissue slices and a plurality of tissue scaffolds joined together to form a layered implant of a desired size and geometry.

16. A method for repairing a tissue injury or defect, comprising:

providing (i) a biocompatible tissue implant comprising a biological tissue slice having a geometry suitable for implantation at a tissue injury or defect site, the tissue slice being capable of acting as a source of an effective amount of viable cells, and further being dimensioned so that the cells can migrate out of the tissue slice to proliferate and integrate with tissue at the tissue injury or defect site and (ii) at least one minced tissue fragment containing a plurality of viable cells;

associating the at least one minced tissue fragment with the tissue slice; and delivering the implant to the tissue site to be repaired.

17. The method of claim 16, wherein the biocompatible tissue implant is in the form of a plurality of tissue slices joined together to form a layered implant of a desired size and geometry.

18. The method of claim 16, further including the step of applying the tissue slice to a biocompatible tissue scaffold to form a composite implant prior to the delivering step, and the step of delivering the implant comprises delivering the composite implant to the tissue site to be repaired.

* * * * *